United States Patent [19]

Fitzjohn et al.

[11] Patent Number: 5,684,011
[45] Date of Patent: Nov. 4, 1997

[54] PYRIMIDINE DERIVATIVES USEFUL AS NEMATICIDES

[75] Inventors: Steven Fitzjohn, Bracknell; Michael Peter Robinson, Henley on Thames; Michael Drysdale Turnbull, Reading, all of England

[73] Assignee: Zeneca Limited, London, England

[21] Appl. No.: 653,099

[22] Filed: May 24, 1996

Related U.S. Application Data

[63] Continuation of Ser. No. 119,920, Sep. 10, 1993, abandoned.

[30] Foreign Application Priority Data

Sep. 16, 1992 [GB] United Kingdom ............... 9219635

[51] Int. Cl.⁶ ..................... A61K 31/505; C07D 239/38
[52] U.S. Cl. ............ 514/274; 514/258; 514/269; 514/272; 544/253; 544/280; 544/283; 544/285; 544/286; 544/309; 544/311; 544/315; 544/316; 544/319; 544/320
[58] Field of Search ...................... 514/258, 269, 514/272, 274; 544/253, 280, 283, 285, 286, 309, 311, 315, 320, 319

[56] References Cited

U.S. PATENT DOCUMENTS

| | | | |
|---|---|---|---|
| 3,223,707 | 12/1965 | Brokke | 544/315 |
| 4,423,047 | 12/1983 | Benneche et al. | 424/251 |
| 5,075,316 | 12/1991 | Hubele | 514/275 |
| 5,246,938 | 9/1993 | Turnbull et al. | 514/274 |

FOREIGN PATENT DOCUMENTS

| | | |
|---|---|---|
| 0033195 | 8/1981 | European Pat. Off. . |
| 0036839 | 9/1981 | European Pat. Off. . |
| 506269 | 9/1992 | European Pat. Off. . |
| 506270 | 9/1992 | European Pat. Off. . |
| 506271 | 9/1992 | European Pat. Off. . |
| 9308180 | 4/1993 | WIPO . |

*Primary Examiner*—Yogendra N. Gupta
*Attorney, Agent, or Firm*—Marian T. Thomson

[57] ABSTRACT

The invention provides novel compounds of formula (I) having nematicidal, insecticidal, acaricidal and fungicidal properties, compositions comprising them and processes and intermediates for their preparation:

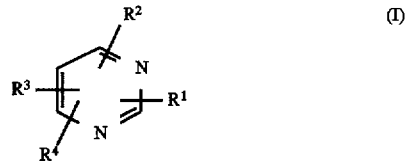

wherein $R^1$ is $-S(O)_n CH_2 CH_2 CH=CF_2$;

n is selected from 0, 1 and 2;

$R^2$, $R^3$, and $R^4$ are independently selected from hydrogen, alkyl, alkenyl, alkynyl, cycloalkyl, alkylcycloalkyl, optionally substituted aryl, optionally substituted arylalkyl, optionally substituted aryloxy, optionally substituted arylalkoxy, alkoxy, alkenyloxy, alkynyloxy, hydroxyalkyl, alkoxyalkyl, alkylthio, alkenylthio, alkynylthio, haloalkyl, haloalkenyl, haloalkynyl, haloalkoxy, haloalkenyloxy, haloalkynyloxy, haloalkylthio, haloalkenylthio, haloalkynylthio, halogen, hydroxy, cyano, nitro, $-NR^5R^6$, $-NR^7COR^8$, $-NR^9SO_2R^{10}$, $-N(SO_2-R^{11})(SO_2-R^{12})$, $-COR^{13}$, $-CONR^{14}R^{15}$, $-COOR^{16}$, $-OCOR^{17}$, $-OSO_2R^{18}$, $-SO_2NR^{19}R^{20}$, $-SO_2R^{21}$, $-SOR^{22}$, $-CSNR^{23}R^{24}$, $-SiR^{25}R^{26}R^{27}$, $-OCH_2CO_2R^{28}$, $-OCH_2CH_2CO_2R^{29}$, $-CONR^{30}SO_2R^{31}$, $-SO_2Z$, or an adjacent pair of $R^2$, $R^3$ and $R^4$ when taken together form a fused 5- or 6-membered carbocyclic or heterocyclic ring;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ are independently selected from hydrogen, alkyl, alkenyl, alkynyl, haloalkyl, haloalkenyl, haloalkynyl, optionally substituted aryl and optionally substituted arylalkyl; and Z is halogen.

13 Claims, No Drawings

PYRIMIDINE DERIVATIVES USEFUL AS NEMATICIDES

This application is a continuation of application Ser. No. 08/119,920, filed Sep. 10, 1993 abandoned.

The present invention relates to novel pyrimidine derivatives having nematicidal, insecticidal, acaricidal and fungicidal activity, to processes for their preparation, to compositions containing them, to methods for killing or controlling nematode, insect or acarid pests using them, and to methods of combating fungi using them.

U.S. Pat. No. 5,075,316 and European Patent Application Nos 36389 and 33195 disclose pyrimidine compounds carrying thio-linked substituents in a variety of contexts. None of these specifically discloses fluoroalkenylthio-substituted pyrimidines or nematicidal activity. U.S. Pat. No. 3,223,707 discloses activity against Meloidgyne spp. for 2-(3,4,4-trifluorobut-3-enylthio)pyrimidine and lower alkyl substituted derivatives. The present invention relates to novel (4,4-difluorobut-3-enylthio)-substituted pyrimidines and oxidised derivatives thereof which exhibit significantly improved levels of nematicidal activity across a wide spectrum of nematode pests, as well as insecticidal activity (including systemic activity) and fungicidal activity.

According to the present invention there is provided a compound of Formula (I) wherein $R^1$ is $-S(O)_n CH_2CH_2CH=CF_2$;

n is selected from 0, 1 and 2;

$R^2$, $R^3$, and $R^4$ are independently selected from hydrogen, alkyl, alkenyl, alkynyl, cycloalkyl, alkylcycloalkyl, optionally substituted aryl, optionally substituted arylalkyl, optionally substituted aryloxy, optionally substituted arylalkoxy, alkoxy, alkenyloxy, alkynyloxy, hydroxyalkyl, alkoxyalkyl, alkylthio, alkenylthio, alkynylthio, haloalkyl, haloalkenyl, haloalkynyl, haloalkoxy, haloalkenyloxy, haloalkynyloxy, haloalkylthio, haloalkenylthio, haloalkynylthio, halogen, hydroxy, cyano, nitro, $-NR^5R^6$, $-NR^7COR^8$, $-NR^9SO_2R^{10}$, $-N(SO_2-R^{11})(SO_2-R^{12})-COR^{13}$, $-CONR^{14}R^{15}$, $-COOR^{16}$, $-OCOR^{17}$, $-OSO_2R^{18}$, $-SO_2NR^{19}R^{20}$, $-SO_2R^{21}$, $-SOR^{22}$, $-CSNR^{23}R^{24}$, $-SiR^{25}R^{26}R^{27}$, $-OCH_2CO_2R^{28}$, $-OCH_2CH_2CO_2R^{29}$, $-CONR^{30}SO_2R^{31}$, $-SO_2Z$, or an adjacent pair of $R^2$, $R^3$ and $R^4$ when taken together form a fused 5- or 6-membered carbocyclic or heterocyclic ring;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ are independently selected from hydrogen, alkyl, alkenyl, alkynyl, haloalkyl, haloalkenyl, haloalkynyl, optionally substituted aryl and optionally substituted arylalkyl; and Z is halogen.

When any one of $R^2$ to $R^{31}$ is an alkyl group it may be straight or branched chain and is preferably $C_{1-6}$ alkyl, and in particular $C_{1-4}$ alkyl, for example methyl, ethyl, propyl, iso-propyl, n-butyl, iso-butyl, sec-butyl or t-butyl.

When any one of $R^2$ to $R^{31}$ is an alkenyl or alkynyl group it may be straight or branched chain and is preferably $C_{2-6}$ alkenyl or $C_{2-6}$ alkynyl, for example vinyl, allyl, but-3-enyl, 3-methyl-but-3-enyl, ethynyl or propargyl.

When any one of $R^2$ to $R^4$ is a cycloalkyl or alkylcycloalkyl group, it is preferably $C_{3-6}$ cycloalkyl or $C_{4-7}$ alkylcycloalkyl, for example, cyclopropyl, cyclopentyl, cyclohexyl or methylcyclopropyl.

When any one of $R^2$ to $R^{31}$ is an optionally substituted aryl or an optionally substituted arylalkyl group, it is preferably an optionally substituted phenyl group or an optionally substituted phenyl-$C_{1-2}$-alkyl group, wherein the preferred optional substitution is one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example phenyl, benzyl, 4-methylphenyl, 4-chlorophenyl, 4-fluorophenyl, 4-nitrophenyl, 3-trifluoromethylphenyl, 4-trifluoromethylphenyl, 4-chlorobenzyl, 4-fluorobenzyl, 3-trifluoromethylbenzyl, 4-trifluoromethylbenzyl, 4-nitrobenzyl or 4-methylbenzyl.

When any one of $R^2$ to $R^4$ is an optionally substituted aryloxy or an optionally substituted arylalkoxy group, it is preferably optionally substituted phenoxy or optionally substituted phenyl-$C_{1-2}$-alkoxy, group, wherein the preferred optional substitution is one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example phenoxy, benzoxy, 4-methylphenoxy, 4-chlorophenoxy, 4-fluorophenoxy, 4-nitrophenoxy, 3-trifluoromethylphenoxy, 4-trifluoromethylphenoxy 4-chlorobenzoxy, 4-fluorobenzoxy, 3-trifluoromethylbenzoxy, 4-trifluoromethylbenzoxy, 4-nitrobenzoxy or 4-methylbenzoxy.

When any one of $R^2$ to $R^{31}$ is a haloalkyl, haloalkenyl or haloalkynyl group, it may contain one or more halogen atoms selected from chlorine, fluorine or bromine, and the alkyl, alkenyl or alkynyl moiety may be straight or branched chain and is preferably $C_{1-6}$ alkyl, especially $C_{1-4}$ alkyl, $C_{2-6}$ alkenyl or $C_{2-6}$ alkynyl, for example, fluoromethyl, difluoromethyl, trifluoromethyl, chloromethyl, dichloromethyl, trichloromethyl, 2-fluoroethyl, 2,2,2-trifluoroethyl, pentafluoroethyl, 2,2-difluoroethenyl, 3,3-dichloroprop-2-enyl, 2-chloroprop-2-enyl, 3,4,4-trifluorobut-3-enyl, 4-fluorobut-3-enyl, 4,4-difluorobut-3-enyl or 3-methyl-4,4-difluorobut-3-enyl.

When any one of $R^2$ to $R^4$ is an alkoxy, alkenyloxy, alkynyloxy, hydroxyalkyl or alkoxyalkyl group it may be straight or branched chain and is preferably $C_{1-6}$ alkoxy, for example methoxy, ethoxy, n-propoxy, iso-propoxy, n-butoxy, iso-butoxy, sec-butoxy or t-butoxy, $C_{2-6}$ alkenyloxy, for example vinyloxy, allyloxy, but-3-enyloxy or 3-methylbut-3-enyloxy, $C_{2-6}$ alkynyloxy, for example propargyloxy, hydroxy-$C_{1-6}$-alkyl, for example hydroxymethyl, 2-hydroxyethyl or 3-hydroxypropyl, $C_{2-6}$ alkoxyalkyl, for example methoxymethyl, methoxyethyl or ethoxymethyl, or $C_{3-6}$ dialkoxyalkyl, for example dimethoxymethyl or diethoxymethyl.

When any one of $R^2$ to $R^4$ is a haloalkoxy group, a haloalkenyloxy group or a haloalkynyloxy group, it may contain one or more halogen atoms selected from chlorine, fluorine or bromine, and the alkoxy, alkenyloxy or alkynyloxy moiety may be straight or branched chain and is preferably $C_{1-6}$ alkoxy, $C_{2-6}$ alkenyloxy or $C_{2-6}$ alkynyloxy, for example, trichloromethoxy, fluoromethoxy, difluoromethoxy, trifluoromethoxy, 2-fluoroethoxy, 2,2,2-trifluoroethoxy, pentafluoroethoxy, 1,1,2,2-tetrafluoroethoxy, 2,2-difluoroethenyloxy, 3,4,4-trifluorobut-3-enyloxy, 4-fluorobut-3-enyloxy, 4,4-difluorobut-3-enyloxy, 3-methyl-4,4-difluorobut-3-enyloxy, 2-chloroprop-2-enyloxy or 3,3-dichloroprop-2-enyloxy.

When any one of $R^2$ to $R^4$ is an alkylthio group, an alkenylthio group or an alkynylthio group, the alkyl, alkenyl or alkynyl moiety is preferably $C_{1-6}$ alkyl, especially $C_{1-4}$ alkyl, $C_{2-6}$ alkenyl or $C_{2-6}$ alkynyl, for example methylthio, ethylthio, n-propylthio, iso-propylthio, n-butylthio, iso-butylthio, sec-butylthio, t-butylthio, allylthio, but-3-enylthio, 3-methylbut-3-enylthio or propargylthio.

When any one of $R^2$ to $R^4$ is a haloalkylthio group, a haloalkenylthio group or a haloalkynylthio group, it may contain one or more halogen atoms selected from chlorine, fluorine or bromine, and the alkyl, alkenyl or alkynyl moiety is preferably $C_{1-6}$ alkyl, especially $C_{1-4}$ alkyl, $C_{2-6}$ alkenyl or $C_{2-6}$ alkynyl, for example fluoromethylthio, difluoromethylthio, trifluoromethylthio, trichloromethylthio, 2-fluoroethylthio, 2,2,2-trifluoroethylthio, 3-fluoro-n-propylthio, pentafluoroethylthio, 2-chloroprop-2-enylthio, 3,3-dichloroprop-2-enylthio, 3,4,4-trifluorobut-3-enylthio, 4-fluorobut-3-enylthio, 4,4-difluorobut-3-enylthio or 3-methyl-4,4-difluorobut-3-enylthio.

When any one of $R^2$ to $R^4$ is halogen, it is preferably fluorine, chlorine, bromine or iodine.

When any one of $R^2$ to $R^4$ is the group —$NR_5R_6$ it is preferably —$NH_2$, a $C_{1-6}$ alkylamino group, for example methylamino or ethylamino, or a di-($C_{1-6}$ alkyl)-amino group, for example dimethylamino or diethylamino.

When any one of $R^2$ to $R^4$ is the group —$NR^7COR^8$ it is preferably, —NHCHO, a $C_{2-6}$ acylamino group or an optionally substituted benzamido group, for example —$NHCOCH_3$, —$NHCOC_2H_5$, benzamido or benzamido optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro.

When any one of $R^2$ to $R^4$ is the group —$NR^9SO_2R^{10}$ it is preferably a $C_{1-6}$ alkanesulphonamido group, for example —$NHSO_2CH_3$ or —$NHSO_2C_2H_5$.

When any one of $R^2$ to $R^4$ is the group —$N(SO_2R^{11})(SO_2R^{12})$ it is preferably a di-($C_{1-6}$ alkanesulphonyl)amino group, for example —$N(SO_2CH_3)_2$ or —$N(SO_2C_2H_5)_2$.

When any one of $R^2$ to $R^4$ is the group —$COR^{13}$, it is preferably formyl, a $C_{2-6}$ acyl group or an optionally substituted benzoyl group, for example acetyl, propionyl, n-butanoyl, benzoyl or benzoyl optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example 4-chlorobenzoyl, 4-fluorobenzoyl, 4-bromobenzoyl, 4-methylbenzoyl or 4-trifluoromethylbenzoyl.

When any one of $R^2$ to $R^4$ is the group —$CONR^{14}R^{15}$, it is preferably —$CONH_2$, an N-($C_{1-6}$ alkyl)-carboxamido group, for example —$CONHCH_3$, —$CONHC_2H_5$ or —$CONHCH_2CH_2CH_3$, or an N,N-di-($C_{1-6}$ alkyl)-carboxamido group, for example —$CON(CH_3)_2$, —$CON(CH_3)(C_2H_5)$ or —$CON(C_2H_5)_2$.

When any one of $R^2$ to $R^4$ is the group —$COOR^{16}$, it is preferably —COOH, a $C_{1-6}$ alkoxycarbonyl group, for example methoxycarbonyl or ethoxycarbonyl, a $C_{1-6}$ haloalkoxycarbonyl group, for example 2-fluoroethoxycarbonyl, or a $C_{2-6}$ haloalkenyloxycarbonyl group, for example 3,4,4-trifluorobut-3-enyloxycarbonyl, 4-fluorobut-3-enyloxycarbonyl, 4,4-difluorobut-3-enyloxycarbonyl or 3-methyl-4,4-difluorobut-3-enyloxycarbonyl, When any one of $R^2$ to $R^4$ is the group —$OCOR^{17}$, it is preferably a $C_{2-6}$ acyloxy group or an optionally substituted benzoyloxy, for example —$OCOCH_3$, —$OCOC_2H_5$, benzoyloxy or benzoyloxy optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro.

When any one of $R^2$ to $R^4$ is the group —$OSO_2R^{18}$, it is preferably a $C_{1-6}$ alkanesulphonyloxy group or an optionally substituted benzenesulphonyloxy group, for example methanesulphonyloxy, ethanesulphonyloxy, benzenesulphonyloxy or benzenesulphonyloxy optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example 4-methylbenzenesulphonyloxy.

When any one of $R^2$ to $R^4$ is the group —$SO_2NR^{19}R^{20}$, it is preferably —$SO_2NH_2$, a $C_{1-6}$ alkylaminosulphonyl group, for example —$SO_2NHCH_3$ or —$SO_2NHC_2H_5$, or a di-($C_{1-6}$ alkyl)-aminosulphonyl group, for example —$SO_2N(CH_3)_2$ or —$SO_2N(C_2H_5)_2$.

When any one of $R^2$ to $R^4$ is the group —$SO_2R^{21}$, it is preferably a $C_{1-6}$ alkanesulphonyl group, a $C_{1-6}$ haloalkanesulphonyl group or an optionally substituted benzenesulphonyl group, for example methanesulphonyl, ethanesulphonyl, trifluoromethanesulphonyl, benzenesulphonyl or benzenesulphonyl optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example 4-methylbenzenesulphonyl.

When any one of $R^2$ to $R^4$ is the group —$SOR^{22}$, it is preferably a $C_{1-6}$ alkanesulphinyl group, for example methanesulphinyl or ethanesulphinyl, or a $C_{1-6}$ haloalkanesulphinyl group, for example trifluoromethanesulphinyl.

When any one of $R^2$ to $R^4$ is the group —$CSNR^{23}R^{24}$ it is preferably —$CSNH_2$, —$CSNHCH_3$ or —$CSN(CH_3)_2$.

When any one of $R^2$ to $R^4$ is the group —$SiR^{25}R^{26}R^{27}$, it is preferably a tri-($C_{1-6}$ alkyl)silyl group, for example, trimethylsilyl or triethylsilyl.

When any one of $R^2$ or $R^4$ is the group —$OCH_2CO_2R^{28}$, it is preferably a $C_{1-6}$ alkoxycarbonylmethoxy group, for example methoxycarbonylmethoxy or ethoxycarbonylmethoxy.

When any one of $R^2$ to $R^4$ is the group —$OCH_2CH_2CO_2R^{29}$, it is preferably a $C_{1-6}$ alkoxycarbonylethoxy group, for example methoxycarbonylethoxy or ethoxycarbonylethoxy.

When any one of $R^2$ to $R^4$ is the group —$CONR^{30}SO_2R^{31}$, it is preferably an N-($C_{1-6}$ alkanesulphonyl)carboxamido group or an N-($C_{1-6}$ alkyl)-N-($C_{1-6}$ alkanesulphonyl)carboxamido group, for example N-(methanesulphonyl)carboxamido or N-methyl-N-(methanesulphonyl)carboxamido.

When any one of $R^2$ to $R^4$ is the group —$SO_2Z$, it is preferably —$SO_2F$, —$SO_2Br$ or —$SO_2Cl$.

When an adjacent pair of $R^2$, $R^3$ and $R^4$ taken together form a fused 5- or 6-membered carbocyclic or heterocyclic ring, the pair of substituents taken together is preferably —$(CH_2)_3$—, —$(CH_2)_4$—, —CH=CH—CH=CH—, —O—$CH_2$—O— optionally substituted with one or two halogen atoms, for example —O—CHF—O— or —O—$CF_2$—O—, —O—CH($CH_3$)—O—, —O—C($CH_3$)$_2$—O— or —O—$(CH_2)_2$—O—, and the fused ring formed thereby is preferably a 5- or 6-membered heterocyclic ring containing two oxygen atoms and optionally substituted with one or more halogen or methyl groups, or a 5- or 6-membered carbocyclic ring.

Accordingly, the invention provides, in a further aspect, a compound of formula (I) wherein $R^1$ is —$S(O)_nCH_2CH_2CH=CF_2$;

n is 0, 1 or 2;

$R^2$, $R^3$, and $R^4$ are independently selected from hydrogen, $C_{1-6}$ alkyl, $C_{2-6}$ alkenyl, $C_{2-6}$ alkynyl, $C_{3-6}$ cycloalkyl, $C_{4-7}$ alkylcycloalkyl, phenyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, phenyl-$C_{1-2}$-alkyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, phenoxy optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, phenyl-$C_{1-2}$-alkoxy optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, $C_{1-6}$ alkoxy, $C_{2-6}$ alkenyloxy, $C_{2-6}$ alkynyloxy, hydroxy-$C_{1-6}$-alkyl, $C_{2-6}$ alkoxyalkyl, C3-6 dialkoxyalkyl, $C_{1-6}$ alkylthio, $C_{2-6}$ alkenylthio, $C_{2-6}$ alkynylthio, $C_{1-6}$ haloalkyl, $C_{2-6}$ haloalkenyl, $C_{2-6}$ haloalkynyl, $C_{1-6}$ haloalkoxy, $C_{2-6}$ haloalkenyloxy, $C_{2-6}$ haloalkynyloxy, $C_{1-6}$ haloalkylthio, $C_{2-6}$ haloalkenylthio, $C_{2-6}$ haloalkynylthio, halogen, hydroxy, cyano, nitro, —$NR^5R^6$, —$NR^7COR^8$, —$NR^9SO_2R^{10}$, —$N(SO_2—R^{11})(SO_2—R^{12})$, —$COR^{13}$, —$CONR^{14}R^{15}$, —$COOR^{16}$, —$OCOR^{17}$, —$OSO_2R^{18}$, —$SO_2NR^{19}R^{20}$, —$SO_2R^{21}$, —$SOR^{22}$, —$CSNR^{23}R^{24}$, —$SiR^{25}R^{26}R^{27}$, —$OCH_2CO_2R^{28}$, —$OCH_2CH_2CO_2R^{29}$, —$CONR^{30}SO_2R^{31}$, —$SO_2Z$, or an adjacent pair of $R^2$, $R^3$ and $R^4$ when taken together form a fused 5- or 6-membered heterocyclic ring containing two oxygen atoms and optionally substituted with one or more halogen or methyl groups, or a 5- or 6-membered carbocyclic ring;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ are independently selected from hydrogen, $C_{1-6}$ alkyl, $C_{2-6}$ alkenyl, $C_{2-6}$ alkynyl, $C_{1-6}$ haloalkyl, $C_{2-6}$ haloalkenyl, $C_{2-6}$ haloalkynyl, phenyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, and benzyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro; and Z is fluoro, chloro or bromo.

A further group of compounds according to the invention which are of particular interest are those of Formula (I) wherein:

$R^1$ is —$S(O)_nCH_2CH_2CH=CF_2$;

n is 0, 1 or 2;

$R^2$, $R^3$, and $R^4$ are independently selected from hydrogen $C_{1-6}$ alkyl such as methyl or ethyl, $C_{2-6}$ alkenyl such as allyl, but-3-enyl or 3-methylbut-3-enyl, $C_{2-6}$ alkynyl such as ethynyl or propargyl, $C_{3-6}$ cycloalkyl such as cyclopropyl, $C_{4-7}$ alkylcycloalkyl such as 1-methylcyclopropyl, phenyl optionally substituted by chloro, fluoro, methyl, ethyl, methoxy, trifluoromethoxy, trifluoromethyl or nitro, such as phenyl, 4-chlorophenyl, 4-fluorophenyl, 3-trifluoromethylphenyl, 4-trifluoromethylphenyl, 4-methylphenyl or 4-nitrophenyl, benzyl optionally substituted by chloro, fluoro, methyl, ethyl, methoxy, trifluoromethoxy, trifluoromethyl or nitro, such as benzyl, 4-chlorobenzyl, 4-fluorobenzyl, 3-trifluoromethylbenzyl, 4-trifluoromethylbenzyl, 4-methylbenzyl or 4-nitrobenzyl, phenoxy optionally substituted by chloro, fluoro, methyl, trifluoromethyl or nitro, such as phenoxy, 4-chlorophenoxy, 4-fluorophenoxy, 3-trifluoromethylphenoxy, 4-trifluoromethylphenoxy, 4-methylphenoxy or 4-nitrophenoxy, benzoxy optionally substituted by chloro, fluoro, methyl, trifluoromethyl or nitro, such as benzoxy, 4-chlorobenzoxy, 4-fluorobenzoxy, 3-trifluoromethylbenzoxy, 4-trifluoromethylbenzoxy, 4-methylbenzoxy or 4-nitrobenzoxy, $C_{1-4}$ alkoxy such as methoxy, ethoxy, iso-propoxy, n-propoxy or sec-butoxy, $C_{2-6}$ alkenyloxy such as allyloxy, but-3-enyloxy or 3-methylbut-3-enyloxy, $C_{2-4}$ alkynyloxy such as propargyloxy, hydroxy-$C_{1-4}$-alkyl such as hydroxymethyl, 2-hydroxyethyl or 3-hydroxypropyl, $C_{2-4}$ alkoxyalkyl such as methoxymethyl, ethoxymethyl, methoxyethyl, $C_{3-6}$ dialkoxyalkyl such as dimethoxymethyl, $C_{1-4}$ alkylthio such as methylthio or ethylthio, $C_{2-6}$ alkenylthio such as allylthio, but-3-enylthio or 3-methylbut-3-enylthio, $C_{2-4}$ alkynylthio such as propargylthio, $C_{1-4}$ fluoroalkyl such as fluoromethyl, difluoromethyl, trifluoromethyl or 2-fluoroethyl, $C_{1-4}$ chloroalkyl such as chloromethyl, dichloromethyl or trichloromethyl, $C_{2-6}$ fluoroalkenyl such as 2,2-difluoroethenyl, 3,4,4-trifluorobut-3-enyl, 4,4-difluorobut-3-enyl or 4,4-difluoro-3-methylbut-3-enyl, $C_{2-4}$ chloroalkenyl such as 3,3-dichloroprop-2-enyl or 2-chloroprop-2-enyl, $C_{1-4}$ fluoroalkoxy such as fluoromethoxy, difluoromethoxy, trifluoromethoxy, 2-fluoroethoxy or 1,1,2,2-tetrafluoroethoxy, $C_{1-4}$ chloroalkoxy such as trichloromethoxy, $C_{2-6}$ fluoroalkenyloxy such as 3,4,4-trifluorobut-3-enyloxy, 4,4-difluorobut-3-enyloxy or 4,4-difluoro-3-methylbut-3-enyloxy, $C_{2-4}$ chloroalkenyloxy such as 2-chloroprop-2-enyloxy or 3,3-dichloroprop-2-enyloxy, $C_{1-4}$ fluoroalkylthio such as fluoromethylthio, difluoromethylthio, trifluoromethylthio or 2-fluoroethylthio, $C_{1-4}$ chloroalkylthio such as trichloromethylthio, $C_{2-6}$ fluoroalkenylthio such as 3,4,4-trifluorobut-3-enylthio, 4,4-difluorobut-3-enylthio or 4,4-difluoro-3-methylbut-3-enylthio, $C_{2-4}$ chloroalkenylthio such as 2-chloroprop-2-enylthio or 3,3-dichloroprop-2-enylthio, chloro, fluoro, bromo, iodo, hydroxy, cyano, nitro, amino, —$NHR^5$ where $R^5$ is $C_{1-4}$ alkyl, such as methylamino or ethylamino, —$NR^5R^6$ where $R^5$ and $R^6$ are $C_{1-4}$ alkyl such as dimethylamino or diethylamino, —$NR^7COR^8$ where $R^7$ is hydrogen and $R^8$ is hydrogen or $C_{1-4}$ alkyl, such as formamido, acetamido, propionamido or benzamido, —$NR^9SO_2R^{10}$ where $R^9$ is hydrogen and $R^{10}$ is $C_{1-4}$ alkyl, such as methanesulphonamido or ethanesulphonamido, —$N(SO_2—R^{11})(SO_2—R^{12})$ where $R^{11}$ and $R^{12}$ are $C_{1-4}$ alkyl such as N,N-di-(methanesulphonyl)amino or N,N-di-(ethanesulphonyl)amino, —$COR^{13}$ where $R^{13}$ is hydrogen or $C_{1-4}$ alkyl such formyl, acetyl or propionyl, —CONR$^{14}$R$^{15}$ where R$^{14}$ and R$^{15}$ are hydrogen or C$_{1-4}$ alkyl, such as carboxamido, N-methylcarboxamido, N-ethylcarboxamido, N,N-dimethylcarboxamido, N-methyl-N-ethylcarboxamido, N,N-diethylcarboxamido or N-(n-propyl)carboxamido, —COOR$^{16}$ where R$^{16}$ is hydrogen, C$_{1-4}$ alkyl, C$_{1-4}$ haloalkyl or C$_{2-6}$ fluoroalkenyl, such as —COOH, 2-fluoroethoxycarbonyl, methoxycarbonyl, ethoxycarbonyl, 3,4,4-trifluorobut-3-enyloxycarbonyl, 3-methyl-4,4-difluorobut-3-enyloxycarbonyl or 4,4-difluorobut-3-enyloxycarbonyl, —OCOR$^{17}$ where R$^{17}$ is C$_{1-4}$ alkyl such as methoxycarbonyloxy or ethoxycarbonyloxy, —OSO$_2$R$^{18}$ where R$^{18}$ is C$_{1-4}$ alkyl such as methanesulphonyloxy or ethanesulphonyloxy, —SO$_2$NR$^{19}$R$^{20}$ where R$^{19}$ and R$^{20}$ are hydrogen or C$_{1-4}$ alkyl such as —SO$_2$NH$_2$, N,N-dimethylaminosulphonyl or N,N-diethylaminosulphonyl, —SO$_2$R$^{21}$ where R$^{21}$ is C$_{1-4}$ alkyl or C$_{1-4}$ haloalkyl such as methanesulphonyl, ethanesulphonyl or trifluoromethanesulphonyl, —SOR$^{22}$ where R$^{22}$ is C$_{1-4}$ alkyl or C$_{1-4}$ haloalkyl such as methanesulphinyl, ethanesulphinyl or trifluoromethanesulphinyl, —CSNR$^{23}$R$^{24}$ where R$^{23}$ and R$^{24}$ are hydrogen or C$_{1-4}$ alkyl such as —CSNH$_2$, —CSNH(CH$_3$) or —CSN(CH$_3$)$_2$, —SiR$^{25}$R$^{26}$R$^{27}$ where R$^{25}$, R$^{26}$ and R$^{27}$ are C$_{1-4}$ alkyl such as trimethylsilyl, —OCH$_2$CO$_2$R$^{28}$ where R$^{28}$ is C$_{1-4}$ alkyl such as —OCH$_2$CO$_2$CH$_3$ or —OCH$_2$CO$_2$CH$_2$CH$_3$, where R$^{30}$ is hydrogen and R$^{31}$ is C$_{1-4}$ alkyl such as N-(methanesulphonyl)-carboxamido, —SO$_2$F, or where an adjacent pair of R$^2$, R$^3$ and R$^4$ taken together are —(CH$_2$)$_3$—, —(CH$_2$)$_4$—, —CH═CH—CH═CH—, —O—CH$_2$—O— optionally substituted with one or two halogen atoms, for example —O—CHF—O— or —O—CF$_2$—O—, —O—CH(CH$_3$)—O—, —O—C(CH$_3$)$_2$—O— or —O—(CH$_2$)$_2$—O—.

A further group of compounds according to the invention which are of particular interest are those of Formula (I) wherein:

R$^1$ is —S(O)$_n$CH$_2$CH$_2$CH═CF$_2$;

n is 0, 1 or 2;

R$^2$, R$^3$, and R$^4$ are independently selected from hydrogen, C$_{1-4}$ alkyl such as methyl or ethyl, phenyl optionally substituted by chloro, fluoro, methyl, ethyl, methoxy, trifluoromethoxy, trifluoromethyl or nitro, such as phenyl, 4-chlorophenyl, 4-fluorophenyl, 3-trifluoromethylphenyl, 4-trifluoromethylphenyl, 4-methylphenyl or 4-nitrophenyl, C$_{1-4}$ alkoxy such as methoxy, ethoxy, iso-propoxy, n-propoxy or sec-butoxy, C$_{1-4}$ fluoroalkyl such as fluoromethyl, difluoromethyl, trifluoromethyl or 2-fluoroethyl, C$_{1-4}$ fluoroalkoxy such as fluoromethoxy, difluoromethoxy, trifluoromethoxy, 2-fluoroethoxy or 1,1,2,2-tetrafluoroethoxy, chloro, or —COOR$^{16}$ where R$^{16}$ is C$_{1-4}$ alkyl, such as methoxycarbonyl or ethoxycarbonyl.

The compounds of Formula (I) fall into three categories depending on the position of substitution of the group R$^1$ on the pyrimidine ring. These are illustrated by Formulae (IA), (IB) and (IC). Compounds according to the invention of particular interest are those according to Formula (IA) or Formula (IB) wherein R$^2$–R$^4$, n and Z have any of the meanings given above.

A further group of compounds according to the invention of particular interest are those of Formulae (IA) and (IB) wherein R$^2$–R$^4$, n and Z have any of the meanings given above, with the proviso that at least one of the groups R$^2$–R$^4$ is hydrogen.

A further group of compounds according to the invention of particular interest are those of Formula (I) wherein R$^1$–R$^4$ and Z have any of the meanings given above and n is 0.

Those compounds of Formula (I) in which n is 1 exhibit stereoisomerism at the oxidised sulphur atom. The scope of the invention is to be understood to include all individual isomers of any compound according to the invention, and all isomer mixtures, including racemic mixtures.

Examples of compounds of formula (I) according to the invention are set out in Table I.

TABLE I

| COMPOUND NO | R$^1$ | R$^2$ | R$^3$ | R$^4$ |
|---|---|---|---|---|
| 1 | 4-H | 5-H | 6-H | 2-SCH$_2$CH$_2$CH═CF$_2$ |
| 2 | 4-H | 5-H | 6-H | 2-S(O)CH$_2$CH$_2$CH═CF$_2$ |
| 3 | 4-OCH$_3$ | 5-H | 6-CF$_3$ | 2-SCH$_2$CH$_2$CH═CF$_2$ |
| 4 | 4-C$_6$H$_5$ | 5-H | 6-H | 2-SCH$_2$CH$_2$CH═CF$_2$ |
| 5 | 4-SCH$_2$CH$_2$CH═CF$_2$ | 5-H | 6-H | 2-H |
| 6 | 4-OCH$_2$CH$_3$ | 5-CH$_3$ | 6-H | 2-SCH$_2$CH$_2$CH═CF$_2$ |
| 7 | 4-OCH$_3$ | 5-H | 6-n-C$_3$H$_7$ | 2-SCH$_2$CH$_2$CH═CF$_2$ |
| 8 | 4-OC$_5$H$_{11}$ | 5-H | 6-H | 2-S(O)$_2$CH$_2$CH$_2$CH═CF$_2$ |
| 9 | 4-OC$_4$H$_9$ | 5-H | 6-H | 2-SCH$_2$CH$_2$CH═CF$_2$ |
| 10 | 4-OCH$_2$CH═CHCH$_3$ | 5-H | 6-H | 2-SCH$_2$CH$_2$CH═CF$_2$ |
| 11 | 4-OH | 5-H | 6-n-C$_3$H$_7$ | 2-SCH$_2$CH$_2$CH═CF$_2$ |
| 12 | 4-CF$_3$ | 5-H | 6-H | 2-SCH$_2$CH$_2$CH═CF$_2$ |
| 13 | 4-SCH$_2$CH$_2$CH═CF$_2$ | 5-H | 6-OCH$_2$CF$_3$ | 2-H |
| 14 | 4-CH$_3$ | 5-H | 6-OCH$_2$CH$_3$ | 2-SCH$_2$CH$_2$CH═CF$_2$ |
| 15 | 4-Cl | 5-H | 6-n-C$_3$H$_7$ | 2-SCH$_2$CH$_2$CH═CF$_2$ |
| 16 | 4-OCH$_2$C$_6$H$_5$ | 5-H | 6-H | 2-SCH$_2$CH$_2$CH═CF$_2$ |
| 17 | 4-OCH$_2$CO$_2$CH$_3$ | 5-H | 6-H | 2-SCH$_2$CH$_2$CH═CF$_2$ |
| 18 | 4-n-C$_3$H$_7$ | 5-H | 6-H | 2-SCH$_2$CH$_2$CH═CF$_2$ |
| 19 | 4-OCH$_2$(4-Cl—C$_6$H$_4$) | 5-H | 6-H | 2-SCH$_2$CH$_2$CH═CF$_2$ |
| 20 | 4-OCH$_2$CO$_2$H | 5-H | 6-H | 2-SCH$_2$CH$_2$CH═CF$_2$ |
| 21 | 4-OCH$_2$CF$_3$ | 5-H | 6-CH(CH$_3$)$_2$ | 2-SCH$_2$CH$_2$CH═CF$_2$ |
| 22 | 4-Cl | 5-H | 6-CH(CH$_3$)$_2$ | 2-SCH$_2$CH$_2$CH═CF$_2$ |
| 23 | 4-O(CH$_2$)$_2$CO$_2$CH$_3$ | 5-H | 6-H | 2-SCH$_2$CH$_2$CH═CF$_2$ |

TABLE I-continued

| COMPOUND NO | R$^1$ | R$^2$ | R$^3$ | R$^4$ |
|---|---|---|---|---|
| 24 | 4-OCH$_3$ | 5-H | 6-CH(CH$_3$)$_2$ | 2-SCH$_2$CH$_2$CH=CF$_2$ |
| 25 | 4-CH(CH$_3$)$_2$ | 5-H | 6-H | 2-SCH$_2$CH$_2$CH=CF$_2$ |
| 26 | 4-SCH$_2$CH$_2$CH=CF$_2$ | 5-H | 6-CH$_3$ | 2-C$_6$H$_5$ |
| 27 | 4-SCH$_2$CH$_2$CH=CF$_2$ | 5-H | 6-H | 2-CH$_3$ |
| 28 | 4-OCH$_3$ | —(CH$_2$)$_4$— | | 2-SCH$_2$CH$_2$CH=CF$_2$ |
| 29 | 4-CH$_3$ | 5-H | 6-H | 2-SCH$_2$CH$_2$CH=CF$_2$ |
| 30 | 4-CH$_3$ | 5-H | 6-H | 2-S(O)CH$_2$CH$_2$CH=CF$_2$ |
| 31 | 4-H | 5-C(CH$_3$)$_3$ | 6-H | 2-SCH$_2$CH$_2$CH=CF$_2$ |
| 32 | 4-H | 5-CF$_3$ | 6-H | 2-SCH$_2$CH$_2$CH=CF$_2$ |
| 33 | 4-H | 5-CH(CH$_3$)$_2$ | 6-H | 2-SCH$_2$CH$_2$CH=CF$_2$ |
| 34 | 4-H | 5-Cl | 6-H | 2-SCH$_2$CH$_2$CH=CF$_2$ |
| 35 | 4-H | 5-C$_6$H$_5$ | 6-H | 2-SCH$_2$CH$_2$CH=CF$_2$ |
| 36 | 4-SCH$_2$CH$_2$CH=CF$_2$ | 5-H | 6-H | 2-SCH$_2$CH$_2$CH=CF$_2$ |
| 37 | 4-OCH$_2$CH$_2$CH=CF$_2$ | 5-H | 6-H | 2-SCH$_2$CH$_2$CH=CF$_2$ |
| 38 | 4-H | —(CH$_2$)$_3$— | | 2-SCH$_2$CH$_2$CH=CF$_2$ |
| 39 | 4-CH$_3$ | 5-CH$_3$ | 6-CH$_3$ | 2-SCH$_2$CH$_2$CH=CF$_2$ |
| 40 | 4-SCH$_2$CH$_2$CH=CF$_2$ | 5-CH$_3$ | 6-SCH$_2$CH$_2$CH=CF$_2$ | 2-H |
| 41 | 4-C≡CH | 5-H | 6-H | 2-SCH$_2$CH$_2$CH=CF$_2$ |
| 42 | 4-CN | 5-H | 6-H | 2-SCH$_2$CH$_2$CH=CF$_2$ |
| 43 | 4-(4-F—C$_6$H$_4$) | 5-H | 6-H | 2-SCH$_2$CH$_2$CH=CF$_2$ |
| 44 | 4-(3-F—C$_6$H$_4$) | 5-H | 6-H | 2-SCH$_2$CH$_2$CH=CF$_2$ |
| 45 | 4-(4-CF$_3$—C$_6$H$_4$CH$_2$) | 5-H | 6-H | 2-SCH$_2$CH$_2$CH=CF$_2$ |
| 46 | 4-$^c$C$_3$H$_5$ | 5-H | 6-H | 2-SCH$_2$CH$_2$CH=CF$_2$ |
| 47 | 4-(1-CH$_3$—$^c$C$_3$H$_5$) | 5-H | 6-H | 2-SCH$_2$CH$_2$CH=CF$_2$ |
| 48 | 4-CH$_2$CF$_3$ | 5-H | 6-H | 2-SCH$_2$CH$_2$CH=CF$_2$ |
| 49 | 4-OCH$_2$CF$_3$ | 5-H | 6-Cl | 2-SCH$_2$CH$_2$CH=CF$_2$ |
| 50 | 4-CH$_2$OCH$_3$ | 5-H | 6-H | 2-SCH$_2$CH$_2$CH=CF$_2$ |
| 51 | 4-Cl | 5-H | 6-Cl | 2-SCH$_2$CH$_2$CH=CF$_2$ |
| 52 | 4-SCH$_2$CH$_2$CH=CF$_2$ | 5-H | 6-OCH$_2$CH$_2$CH=CF$_2$ | 2-H |
| 53 | 4-F | 5-H | 6-H | 2-SCH$_2$CH$_2$CH=CF$_2$ |
| 54 | 4-SCH$_3$ | 5-H | 6-F | 2-SCH$_2$CH$_2$CH=CF$_2$ |
| 55 | 4-C(CH$_3$)$_3$ | 5-H | 6-H | 2-SCH$_2$CH$_2$CH=CF$_2$ |
| 56 | 4-C(CH$_3$)$_3$ | 5-H | 6-H | 2-S(O)CH$_2$CH$_2$CH=CF$_2$ |
| 57 | 4-H | —CH=CH—CH=CH— | | 2-SCH$_2$CH$_2$CH=CF$_2$ |
| 58 | 4-H | —CH=CH—CH=CH— | | 2-S(O)CH$_2$CH$_2$CH=CF$_2$ |
| 59 | 4-H | —CH=CH—CH=CH— | | 2-S(O)$_2$CH$_2$CH$_2$CH=CF$_2$ |
| 60 | 4-OH | —CH=CH—CH=CH— | | 2-SCH$_2$CH$_2$CH=CF$_2$ |
| 61 | 4-CF$_2$CF$_3$ | 5-H | 6-H | 2-SCH$_2$CH$_2$CH=CF$_2$ |
| 62 | 4-CH(OCH$_3$)$_2$ | 5-H | 6-H | 2-SCH$_2$CH$_2$CH=CF$_2$ |
| 63 | 4-Cl | 5-H | 6-H | 2-SCH$_2$CH$_2$CH=CF$_2$ |
| 64 | 4-NH$_2$ | 5-NH$_2$ | 6-H | 2-SCH$_2$CH$_2$CH=CF$_2$ |
| 65 | 4-OCH$_2$CF$_3$ | 5-H | 6-H | 2-SCH$_2$CH$_2$CH=CF$_2$ |
| 66 | 4-OCH$_2$CF$_3$ | 5-H | 6-H | 2-S(O)CH$_2$CH$_2$CH=CF$_2$ |
| 67 | 4-OCH$_2$CH=CH$_2$ | 5-H | 6-H | 2-SCH$_2$CH$_2$CH=CF$_2$ |
| 68 | 4-OCH$_2$CH$_2$CH=CF$_2$ | 5-H | 6-CF$_3$ | 2-SCH$_2$CH$_2$CH=CF$_2$ |
| 69 | 4-OCH$_2$CH$_3$ | 5-H | 6-H | 2-SCH$_2$CH$_2$CH=CF$_2$ |
| 70 | 4-OH | 5-H | 6-H | 2-SCH$_2$CH$_2$CH=CF$_2$ |
| 71 | 4-OH | 5-CH$_3$ | 6-H | 2-SCH$_2$CH$_2$CH=CF$_2$ |
| 72 | 4-OH | 5-H | 6-CF$_3$ | 2-SCH$_2$CH$_2$CH=CF$_2$ |
| 73 | 4-OCH(CH$_3$)$_2$ | 5-H | 6-H | 2-SCH$_2$CH$_2$CH=CF$_2$ |
| 74 | 4-OC$_6$H$_5$ | 5-H | 6-H | 2-SCH$_2$CH$_2$CH=CF$_2$ |
| 75 | 4-OCH$_2$CH$_3$ | 5-H | 6-C$_6$H$_5$ | 2-SCH$_2$CH$_2$CH=CF$_2$ |
| 76 | 4-(3-CF$_3$—C$_6$H$_4$) | 5-H | 6-H | 2-SCH$_2$CH$_2$CH=CF$_2$ |
| 77 | 4-(4-NO$_2$—C$_6$H$_4$) | 5-H | 6-H | 2-SCH$_2$CH$_2$CH=CF$_2$ |
| 78 | 4-SCH$_2$CH$_2$CH=CF$_2$ | 5-H | 6-H | 2-SCH$_3$ |
| 79 | 4-CH=CF$_2$ | 5-H | 6-H | 2-SCH$_2$CH$_2$CH=CF$_2$ |
| 80 | 4-CHO | 5-H | 6-H | 2-SCH$_2$CH$_2$CH=CF$_2$ |
| 81 | 4-CONH$_2$ | 5-H | 6-H | 2-SCH$_2$CH$_2$CH=CF$_2$ |
| 82 | 4-COOH | 5-H | 6-H | 2-SCH$_2$CH$_2$CH=CF$_2$ |
| 83 | 4-COOCH$_3$ | 5-H | 6-H | 2-SCH$_2$CH$_2$CH=CF$_2$ |
| 84 | 4-H | 5-NO$_2$ | 6-H | 2-SCH$_2$CH$_2$CH=CF$_2$ |
| 85 | 4-H | 5-SCH$_2$CH$_2$CH=CF$_2$ | 6-H | 2-H |
| 86 | 4-CH$_3$ | 5-CH$_2$C$_6$H$_5$ | 6-H | 2-SCH$_2$CH$_2$CH=CF$_2$ |
| 87 | 4-CH$_3$ | 5-COC$_6$H$_5$ | 6-H | 2-SCH$_2$CH$_2$CH=CF$_2$ |
| 88 | 4-OCH$_2$CCl=CH$_2$ | 5-H | 6-H | 2-SCH$_2$CH$_2$CH=CF$_2$ |
| 89 | 4-OCH$_2$CH=CCl$_2$ | 5-H | 6-H | 2-SCH$_2$CH$_2$CH=CF$_2$ |
| 90 | 4-C$_6$H$_5$ | 5-OC$_2$H$_5$ | 6-H | 2-SCH$_2$CH$_2$CH=CF$_2$ |
| 91 | 4-C$_6$H$_5$ | 5-COOH | 6-H | 2-SCH$_2$CH$_2$CH=CF$_2$ |
| 92 | 4-OH | 5-H | 6-CH$_2$OCH$_3$ | 2-SCH$_2$CH$_2$CH=CF$_2$ |
| 93 | 4-OCH$_3$ | 5-H | 6-H | 2-SCH$_2$CH$_2$CH=CF$_2$ |
| 94 | 4-SCH$_2$CH$_2$CH=CF$_2$ | 5-NO$_2$ | 6-H | 2-SCH$_2$CH$_2$CH=CF$_2$ |
| 95 | 4-SCH$_2$CH$_2$CH=CF$_2$ | —CH=CH—CH=CH— | | 2-H |
| 96 | 4-C$_6$H$_5$ | 5-H | 6-H | 2-S(O)CH$_2$CH$_2$CH=CF$_2$ |
| 97 | 4-C$_6$H$_5$ | 5-H | 6-H | 2-S(O)$_2$CH$_2$CH$_2$CH=CF$_2$ |
| 98 | 4-SCH$_2$CH$_2$CH=CF$_2$ | 5-H | 6-SCH$_2$CH$_2$CH=CF$_2$ | 2-H |
| 99 | 4-SCH$_2$CH$_2$F | 5-H | 6-H | 2-SCH$_2$CH$_2$CH=CF$_2$ |

TABLE I-continued

| COMPOUND NO | R$^1$ | R$^2$ | R$^3$ | R$^4$ |
|---|---|---|---|---|
| 100 | 4-(3-CF$_3$—C$_6$H$_4$) | 5-H | 6-H | 2-S(O)CH$_2$CH$_2$CH=CF$_2$ |
| 101 | 4-(3-CF$_3$—C$_6$H$_4$) | 5-H | 6-H | 2-S(O)$_2$CH$_2$CH$_2$CH=CF$_2$ |
| 102 | 4-(4-F—C$_6$H$_4$) | 5-H | 6-H | 2-S(O)CH$_2$CH$_2$CH=CF$_2$ |
| 103 | 4-(4-F—C$_6$H$_4$) | 5-H | 6-H | 2-S(O)$_2$CH$_2$CH$_2$CH=CF$_2$ |
| 104 | 4-(4-NO$_2$—C$_6$H$_4$) | 5-H | 6-H | 2-S(O)CH$_2$CH$_2$CH=CF$_2$ |
| 105 | 4-(4-NO$_2$—C$_6$H$_4$) | 5-H | 6-H | 2-S(O)$_2$CH$_2$CH$_2$CH=CF$_2$ |
| 106 | 4-CF$_2$CF$_3$ | 5-H | 6-H | 2-S(O)CH$_2$CH$_2$CH=CF$_2$ |
| 107 | 4-CF$_2$CF$_3$ | 5-H | 6-H | 2-S(O)$_2$CH$_2$CH$_2$CH=CF$_2$ |
| 108 | 4-CN | 5-H | 6-H | 2-S(O)CH$_2$CH$_2$CH=CF$_2$ |
| 109 | 4-CN | 5-H | 6-H | 2-S(O)$_2$CH$_2$CH$_2$CH=CF$_2$ |
| 110 | 4-H | 5-Cl | 6-H | 2-S(O)CH$_2$CH$_2$CH=CF$_2$ |
| 111 | 4-H | 5-Cl | 6-H | 2-S(O)$_2$CH$_2$CH$_2$CH=CF$_2$ |
| 112 | 4-H | 5-OCH$_2$CF$_3$ | 6-H | 2-SCH$_2$CH$_2$CH=CF$_2$ |
| 113 | 4-H | 5-OCH$_2$CF$_3$ | 6-H | 2-S(O)CH$_2$CH$_2$CH=CF$_2$ |
| 114 | 4-H | 5-OCH$_2$CF$_3$ | 6-H | 2-S(O)$_2$CH$_2$CH$_2$CH=CF$_2$ |
| 115 | 4-H | 5-OCH$_2$CH$_2$F | 6-H | 2-SCH$_2$CH$_2$CH=CF$_2$ |
| 116 | 4-H | 5-OCH$_2$CH$_2$F | 6-H | 2-S(O)CH$_2$CH$_2$CH=CF$_2$ |
| 117 | 4-H | 5-OCH$_2$CH$_2$F | 6-H | 2-S(O)$_2$CH$_2$CH$_2$CH=CF$_2$ |
| 118 | 4-H | 5-OCH$_2$CH$_3$ | 6-H | 2-SCH$_2$CH$_2$CH=CF$_2$ |
| 119 | 4-H | 5-OCH$_2$CH$_3$ | 6-H | 2-S(O)CH$_2$CH$_2$CH=CF$_2$ |
| 120 | 4-H | 5-OCH$_2$CH$_3$ | 6-H | 2-S(O)$_2$CH$_2$CH$_2$CH=CF$_2$ |
| 121 | 4-H | 5-OCH$_3$ | 6-H | 2-SCH$_2$CH$_2$CH=CF$_2$ |
| 122 | 4-H | 5-OCH$_3$ | 6-H | 2-S(O)CH$_2$CH$_2$CH=CF$_2$ |
| 123 | 4-H | 5-OCH$_3$ | 6-H | 2-S(O)$_2$CH$_2$CH$_2$CH=CF$_2$ |
| 124 | 4-OC$_6$H$_5$ | 5-H | 6-H | 2-S(O)CH$_2$CH$_2$CH=CF$_2$ |
| 125 | 4-OC$_6$H$_5$ | 5-H | 6-H | 2-S(O)$_2$CH$_2$CH$_2$CH=CF$_2$ |
| 126 | 4-OCH$_2$C$_6$H$_5$ | 5-H | 6-H | 2-S(O)CH$_2$CH$_2$CH=CF$_2$ |
| 127 | 4-OCH$_2$C$_6$H$_5$ | 5-H | 6-H | 2-S(O)$_2$CH$_2$CH$_2$CH=CF$_2$ |
| 128 | 4-OCH$_2$CCl=CH$_2$ | 5-H | 6-H | 2-S(O)CH$_2$CH$_2$CH=CF$_2$ |
| 129 | 4-OCH$_2$CCl=CH$_2$ | 5-H | 6-H | 2-S(O)$_2$CH$_2$CH$_2$CH=CF$_2$ |
| 130 | 4-OCH$_2$CF$_3$ | 5-H | 6-OCH$_2$CF$_3$ | 2-SCH$_2$CH$_2$CH=CF$_2$ |
| 131 | 4-OCH$_2$CF$_3$ | 5-H | 6-OCH$_3$ | 2-SCH$_2$CH$_2$CH=CF$_2$ |
| 132 | 4-OCH$_2$CH=CH$_2$ | 5-H | 6-H | 2-S(O)CH$_2$CH$_2$CH=CF$_2$ |
| 133 | 4-OCH$_2$CH=CH$_2$ | 5-H | 6-H | 2-S(O)$_2$CH$_2$CH$_2$CH=CF$_2$ |
| 134 | 4-OCH$_2$CH$_2$CH=CF$_2$ | 5-H | 6-H | 2-S(O)CH$_2$CH$_2$CH=CF$_2$ |
| 135 | 4-OCH$_2$CH$_2$CH=CF$_2$ | 5-H | 6-H | 2-S(O)$_2$CH$_2$CH$_2$CH=CF$_2$ |
| 136 | 4-OCH$_2$CH$_3$ | 5-H | 6-H | 2-S(O)CH$_2$CH$_2$CH=CF$_2$ |
| 137 | 4-OCH$_2$CH$_3$ | 5-H | 6-H | 2-S(O)$_2$CH$_2$CH$_2$CH=CF$_2$ |
| 138 | 4-OCH$_3$ | 5-H | 6-H | 2-S(O)CH$_2$CH$_2$CH=CF$_2$ |
| 139 | 4-OCH$_3$ | 5-H | 6-H | 2-S(O)$_2$CH$_2$CH$_2$CH=CF$_2$ |
| 140 | 4-OCH$_3$ | 5-H | 6-OCH$_3$ | 2-SCH$_2$CH$_2$CH=CF$_2$ |
| 141 | 4-OH | 5-H | 6-OH | 2-SCH$_2$CH$_2$CH=CF$_2$ |
| 142 | 4-S(O)$_2$CH$_2$CH$_2$CH=CF$_2$ | 5-H | 6-H | 2-H |
| 143 | 4-S(O)$_2$CH$_2$CH$_2$CH=CF$_2$ | 5-H | 6-OCH$_2$CF$_3$ | 2-H |
| 144 | 4-S(O)$_2$CH$_2$CH$_2$CH=CF$_2$ | 5-H | 6-OCH$_2$CH$_2$F | 2-H |
| 145 | 4-S(O)$_2$CH$_2$CH$_2$CH=CF$_2$ | 5-H | 6-OCH$_2$CH$_3$ | 2-H |
| 146 | 4-S(O)$_2$CH$_2$CH$_2$CH=CF$_2$ | 5-H | 6-OCH$_3$ | 2-H |
| 147 | 4-S(O)CH$_2$CH$_2$CH=CF$_2$ | 5-H | 6-H | 2-H |
| 148 | 4-S(O)CH$_2$CH$_2$CH=CF$_2$ | 5-H | 6-OCH$_2$CF$_3$ | 2-H |
| 149 | 4-S(O)CH$_2$CH$_2$CH=CF$_2$ | 5-H | 6-OCH$_2$CH$_2$F | 2-H |
| 150 | 4-S(O)CH$_2$CH$_2$CH=CF$_2$ | 5-H | 6-OCH$_2$CH$_3$ | 2-H |
| 151 | 4-S(O)CH$_2$CH$_2$CH=CF$_2$ | 5-H | 6-OCH$_3$ | 2-H |
| 152 | 4-SCH$_2$CH$_2$CH=CF$_2$ | 5-H | 6-Cl | 2-H |
| 153 | 4-SCH$_2$CH$_2$CH=CF$_2$ | 5-H | 6-OCH$_2$CF$_3$ | 2-H |
| 154 | 4-SCH$_2$CH$_2$CH=CF$_2$ | 5-H | 6-OCH$_2$CH$_2$F | 2-H |
| 155 | 4-SCH$_2$CH$_2$CH=CF$_2$ | 5-H | 6-OCH$_2$CH$_3$ | 2-H |
| 156 | 4-SCH$_2$CH$_2$CH=CF$_2$ | 5-H | 6-OCH$_3$ | 2-H |
| 157 | 4-SCH$_2$CH$_2$CH=CF$_2$ | 5-H | 6-OH | 2-H |
| 158 | 4-SCH$_2$CH$_2$CH=CF$_2$ | 5-OCH$_2$CF$_3$ | 6-H | 2-H |
| 159 | 4-SCH$_2$CH$_2$CH=CF$_2$ | 5-OCH$_2$CH$_2$F | 6-H | 2-H |
| 160 | 4-SCH$_2$CH$_2$CH=CF$_2$ | 5-OCH$_2$CH$_3$ | 6-H | 2-H |
| 161 | 4-SCH$_2$CH$_2$CH=CF$_2$ | 5-OCH$_3$ | 6-H | 2-H |
| 162 | 4-CH=CH$_2$ | 5-H | 6-H | 2-SCH$_2$CH$_2$CH=CF$_2$ |

$^c$indicates a cyclic substituent.

Compounds of Formula (I) wherein R$^1$, R$^2$, R$^3$, R$^4$ and Z have any of the meanings given above and n is 0, may be prepared by dehydrobromination of the corresponding compound of Formula (III), for example by treatment of the compound of Formula (III) with a base such as an alkali metal hydroxide, for example potassium or sodium hydroxide, or a tertiary amine, for example 1,8-diazabicyclo [5.4.0]undec-7-ene, in the presence of an inert solvent, for example dimethylformamide. Compounds of Formula (III) may be prepared from the corresponding mercapto (thiol) compound of Formula (II) by reaction of the compound of Formula (II) with a compound of Formula (IV), wherein L is a readily displaceable leaving group such as iodo, methanesulphonyloxy and especially para-toluenesulphonyloxy, under conditions well known in the art for such displacement reactions, for example in the presence of a mild base such as an alkali metal carbonate, for example potassium or sodium carbonate, in an inert solvent, at a temperature in the range from 40° C. to 100° C., and most conveniently at the reflux temperature of a suitable inert solvent such as acetone which has a boiling point within this range. Compounds of Formula (IV) may be prepared by the following sequence of reactions. Acrylic acid ($CH_2=CHCO_2H$, commercially available) is reacted with dibromodifluoromethane ($CF_2Br_2$) under the conditions described by Rong and Keese in Tetrahedon Letters, 1990, page 5615, in the presence of acetonitrile, water, sodium dithionite ($Na_2S_2O_4$) and sodium bicarbonate, to give the compound of Formula (V). The compound of Formula (VI) is then prepared by reduction of the compound of Formula (V) under conditions well known in the art for the reduction of an acid group to a primary alcohol, for example using lithium aluminium hydride in the presence of an inert solvent such as tetrahydrofuran. Compounds of Formula (IV) may then be prepared from the compound of Formula (VI) by standard methods for the conversion of a primary hydroxyl group to a displaceable leaving group. In the case of compounds of Formula (IV) where L is methanesulphonyloxy or para-toluenesulphonyloxy, the compound of Formula (VI) may be reacted with methanesulphonyl chloride or para-toluenesulphonyl chloride. In the case of the compound of Formula (IV) where L is iodo, the compound of Formula (VI) may be reacted with an alkali metal iodide, for example sodium or potassium iodide, under acidic conditions.

A preferred method for the preparation of compounds of Formula (I) wherein $R^1$, $R^2$, $R^3$, $R^4$ and Z have any of the meanings given above and n is 0, is by reaction of a compound of Formula (II) with a compound of Formula (VII) wherein $R^a$ is a $C_{1-4}$ alkyl group, especially methyl, or a phenyl group optionally substituted with a $C_{1-4}$ alkyl group, especially para-tolyl, under conditions well known in the art for such displacement reactions, for example in the presence of a mild base such as an alkali metal carbonate, for example potassium or sodium carbonate, in an inert solvent, at a temperature in the range from 40° C. to 100° C., and most conveniently at the reflux temperature of a suitable inert solvent such as acetone which has a boiling point within this range. Compounds of Formula (VII) may be prepared by the following sequence of reactions. Hydrogen bromide is reacted with the commercially available compound of Formula (VIII) under standard conditions for an addition reaction, for example by passing hydrogen bromide gas through a solution of the compound of Formula (VIII) in an inert solvent to give the compound of Formula (IX). The compound of Formula (IX) is then reacted with the silver salt of a sulphonic acid of Formula $R^aSO_3H$, wherein $R^a$ has the meaning given above, for example the silver salt of para-toluenesulphonic acid (silver tosylate), preferably in an inert solvent in the absence of light, to give the corresponding compound of Formula (X). Debromofluorination of the compound of Formula (X), for example by reaction with zinc, preferably in the presence of a suitable catalyst such as iodine, gives the compound (VII), wherein $R^a$ has the meanings given above.

A further method for the preparation of compounds of Formula (I) wherein $R^1$, $R^2$, $R^3$, $R^4$ and Z have any of the meanings given above and n is 0, is provided by reaction of a compound of Formula (II) with the compound of Formula (IX), for example in the presence of a base such as an alkali metal carbonate, for example sodium or potassium carbonate, in an inert solvent, to give the corresponding compound of Formula (XI), wherein $R^2$, $R^3$, $R^4$ and Z have any of the meanings given above. The compound of Formula (XI) may then be converted to the corresponding compound of Formula (I) by a debromofluorination reaction as described above for the preparation of a compound of formula (VII) from the corresponding compound of Formula (X).

A further method of preparation of compounds of formula (I) where $R^1$, $R^2$, $R^3$, $R^4$ and Z have the meanings given above and n is 0 is analogous to that of Hayashi et al, Chemistry Letters, 1979, p983-986 which discloses the reaction of an aldehyde with the appropriately halogenated methane in the presence of zinc dust and triphenylphosphine in dimethylacetamide to give vinyl halides. Thus, the first step comprises reacting a appropriately substituted compound of formula (II) with 2-(2-bromoethyl)-1,3-dioxolane to form the corresponding dioxolane in the presence of a base such as a carbonate, for example, potassium carbonate, and an inert solvent, for example acetone. The second step comprises treating the dioxolane with aqueous acid, for example hydrochloric acid in the presence or absence of an inert co-solvent, for example, tetrahydrofuran, to form the corresponding oxopropylthiopyrimidine. Lastly, the oxopropylthiopyrimidine is then reacted with dibromodifluoromethane in an inert solvent, for example, dimethylacetamide, in the presence of a phosphine agent, for example, triphenylphosphine and zinc dust. Both the compounds of formula (II), 2-(2-bromoethyl)-1,3-dioxolane and dibromodifluoromethane can be obtained by conventional methods as described herein or from commercial sources.

In a further aspect therefore, the invention provides a process for the preparation of a compound of Formula (I) wherein $R^1$, $R^2$, $R^3$, $R^4$ and Z have any of the meanings given hereinbefore and n is 0, which comprises the step of reaction of the corresponding compound of Formula (II) with a compound of Formula (IV) wherein L is a readily displaceable leaving group, to give a compound of Formula (III) followed by the step of dehydrobromination of the compound of Formula (III) in the presence of a base.

In a further aspect the invention provides a process for the preparation of a compound of Formula (I) wherein $R^1$, $R^2$, $R^3$, $R^4$ and Z have any of the meanings given hereinbefore and n is 0, which comprises reaction of a compound of Formula (II) with a compound of Formula (VII) wherein $R^a$ is a $C_{1-4}$ alkyl group or a phenyl group optionally substituted with a $C_{1-4}$ alkyl group.

In a further aspect the invention provides a process for the preparation of a compound of Formula (I) wherein $R^1$, $R^2$, $R^3$, $R^4$ and Z have any of the meanings given hereinbefore and n is 0, which comprises the step of reaction of a compound of Formula (II) with the compound of Formula (IX) to give a compound of Formula (XI), followed by the step of debromofluorination of the compound of Formula (XI).

Many compounds of Formula (I) as described herein may also be prepared from other compounds of Formula (I) by transformation of the appropriate $R^2$, $R^3$ and $R^4$ substituents using standard chemical procedures. Many such procedures are described in the experimental examples, and are often generally applicable to similar transformations, thereby providing by analogy yet further procedures for the preparation of the appropriate compounds of Formula (I).

It will be appreciated by those skilled in the art that compounds of Formula (II) exist in tautomeric equilibrium between the equivalent mercapto and thione forms. For the sake of convenience, the compounds are referred to herein in their mercapto form unless otherwise stated. Similarly, compounds of Formula (I), (IA), (IB), (IC), (II), (III) and (XI) wherein one or more of $R^2$–$R^4$ represents hydroxy in the 2, 4 or 6 position on the pyrimidine ring exist in tautomeric equilibrium between the equivalent hydroxy and keto forms.

Compounds of Formulas (III), (IV), (VII), (X) and (XI) have not been previously reported. In five further aspects, therefore, the invention provides: a compound of Formula (III) wherein $R^2$, $R^3$, $R^4$ and Z have any of the meanings given hereinbefore; a compound of Formula (IV) wherein L is a readily displaceable leaving group, a compound of Formula (VII) wherein $R^a$ is a $C_{1-4}$ alkyl group or a phenyl group optionally substituted with a $C_{1-4}$ alkyl group; a compound of Formula (X) wherein $R^a$ is a $C_{1-4}$ alkyl group or a phenyl group optionally substituted with a $C_{1-4}$ alkyl group; and a compound of Formula (XI) wherein $R^2$, $R^3$, $R^4$ and Z have any of the meanings given hereinbefore.

Compounds of Formula (II) are commercially available or may be prepared from commercially available precursors by standard procedures well known in the art. Typical procedures for the preparation of the relevant compounds of Formula (II) and their precursors may be found in the following standard references: The Pyrimidines, D. J. Brown (Published by Wiley, 1962); The Chemistry of Heterocyclic Compounds, Vol 16, Supplement I and Supplement II (Edited by A. Weissberger). The choice of the most suitable process is dependent upon the particular substitution pattern required and will be readily determined by those skilled in the art from the standard methods. A number of suitable procedures for the preparation of compounds of Formula (II) from readily or commercially available precursor are provided in the experimental examples. Others not exemplified herein may be obtained by procedures analogous to these or by other well known procedures.

An alternative procedure to those described above which is of specific interest for the preparation of compounds of Formula (IA) wherein n is 0 is provided by the direct substitution of the compound of Formula (XII), or preferably a salt thereof, especially a halide salt such as the bromide or iodide salt, or a $C_{1-4}$ alkanesulphonate or a $C_{1-4}$ alkylbenzenesulphonate salt such as the methanesulphonate salt or para-tolylsulphonate salt, for thiourea in standard synthetic procedures for the preparation of pyrimidines by reaction of thiourea and an appropriate bifunctional compound. Examples of such procedures are provided in the experimental examples below. In a further aspect, therefore, the invention provides a compound of Formula (XII) or a halide, $C_{1-4}$ alkanesulphonate or $C_{1-4}$ alkylbenzenesulphonate salt thereof.

The compounds of formula (I) where $R^1$, $R^2$, $R^3$, $R^4$ and Z have the meanings defined above and n is 1 or 2, are prepared by oxidising the correspondingly substituted compound of formula (I) when n is 0, using conventional methods, for example by treatment with a suitable oxidising agent in an inert organic solvent. In general, oxidation of a compound of Formula (I) with one equivalent of a suitable oxidising agent provides the corresponding compound wherein n is 1, and oxidation using two equivalents of the oxidising agent provides the corresponding compound wherein n is 2. Suitable oxidising agents include organic and inorganic peroxides such as peroxy carboxylic acids, or their salts, for example, meta-chloroperbenzoic acid, perbenzoic acid, magnesium monoperoxy-phthalic acid or potassium peroxymono-sulphate or sodium periodate.

Thus, according to a further aspect of the present invention there is provided a process for the preparation of compounds of formula (I) where n is 1 or 2 and $R^1$, $R^2$, $R^3$, $R^4$ and Z have the meanings defined above, which comprises oxidation of the correspondingly substituted compound of formula (I) where n is 0.

The compounds of formula (I) are nematicidal and can be used to control nematodes in crop plants. Therefore, in a further aspect of the invention, there is provided a method for killing or controlling nematodes which comprises applying to the locus of the pests or to a plant susceptible to attack by the pest an effective amount of a compound of formula (I) as defined herein.

The term "controlling" extends to non-lethal effects which result in the prevention of damage to the host plant and the limitation of nematode population increase. These effects may be the result of chemical induced disorientation, immobilisation, or hatch prevention or induction. The chemical treatment may also have deleterious effects on nematode development or reproduction.

The compounds of the invention can be used against both plant-parasitic nematodes and nematodes living freely in the soil. Examples of plant-parasitic nematodes are: ectoparasites, for example Xiphinema spp., Longidorus spp. and Trichodorous spp.; semi-endoparasites, for example, Tylenchulus spp.; migratory endoparasites, for example, Pratylenchus spp., Radopholus spp. and Scutellonema spp.; sedentary endoparasites, for example, Heterodera spp., Globodera spp. and Meloidogyne spp.; and stem and leaf endoparasites, for example, Ditylenchus spp., Aphelenchoides spp. and Hirshmaniella spp.

The compounds of formula (I) display activity against different types of nematodes including the cyst nematode.

The compounds of Formula (I) may also be used to combat and control infestations of insect pests such as lepidoptera, diptera, homoptera and coleoptera (including diabrotica i.e. corn rootworms) and also other invertebrate pests, for example, acarine pests. The insect and acarine pests which may be combated and controlled by the use of the invention compounds include those pests associated with agriculture (which term includes the growing of crops for food and fibre products), horticulture and animal husbandry, forestry, the storage of products of vegetable origin, such as fruit, grain and timber, and also those pests associated with the transmission of diseases of man and animals. Examples of insect and acarine pest species which may be controlled by the compounds of Formula (I) include:

*Myzus persicae* (aphid)
*Aphis gossypii* (aphid)
*Aphis fabae* (aphid)
*Megoura viceae* (aphid)
*Aedes aegypti* (mosquito)
Anopheles spp. (mosquitos)
Culex spp. (mosquitos)
*Dysdercus fasciatus* (capsid)
*Musca domestica* (housefly)
*Pieris brassicae* (white butterfly)
*Plutella maculipennis* (diamond back moth)
*Phaedon cochleariae* (mustard beetle)
Aonidiella spp. (scale insects)
Trialeuroides spp. (white flies)
*Bemisia tabaci* (white fly)
*Blattella germanica* (cockroach)
*Periplaneta americana* (cockroach)
*Blatta orientalis* (cockroach)
*Spodoptera littoralis* (cotton leafworm)
*Heliothis virescens* (tobacco budworm)
*Chortiocetes terminifera* (locust)
Diabrotica spp. (rootworms)
Agrotis spp. (cutworms)
*Chilo partellus* (maize stem borer)
*Nilaparvata lugens* (planthopper)
*Nephotettix cincticeps* (leafhopper)
*Panonychus ulmi* (European red mite)
*Panonychus citri* (citrus red mite)

*Tetranychus urticae* (two-spotted spider mite)
*Tetranychus cinnabarinus* (carmine spider mite)
*Phyllcoptruta oleivora* (citrus rust mite)
*Polyphagotarsonemus latus* (broad mite)
Brevipalpus spp. (mites)

In order to apply the compound to the locus of the nematode, insect or acarid pest, or to a plant susceptible to attack by the nematode, insect or acarid pest, the compound is usually formulated into a composition which includes in addition to the compound of formula (I) suitable inert diluent or carrier materials, and/or surface active agents. Thus in two further aspects of the invention there is provided a nematicidal, insecticidal or acaricidal composition comprising an effective amount of a compound of formula (I) as defined herein and an inert diluent or carrier material and optionally a surface active agent.

The amount of composition generally applied for the control of nematode pests gives a rate of active ingredient from 0.01 to 10 kg per hectare, preferably from 0.1 to 6 kg per hectare.

The compositions can be applied to the soil, plant or seed, to the locus of the pests, or to the habitat of the pests, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, fuller's earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils. with the active ingredient. Other additives may also be included, such as emulsifying agents, wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. To apply the concentrates they are diluted in water and are usually applied by means of a spray to the area to be treated. For agricultural or horticultural purposes, an aqueous preparation containing between 0.0001% and 0.1% by weight of the active ingredient (approximately equivalent to from 5–2000 g/ha) is particularly useful.

Suitable liquid solvents for ECs include methyl ketone, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropyl-naphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogeneous for a sufficient time to enable them to be applied by conventional spray equipment. The concentrates may contain 1–85% by weight of the active ingredient or ingredients. When diluted to form aqueous preparations such preparations may contain varying amounts of the active ingredient depending upon the purpose for which they are to be used.

The compounds of formula (I) may also be formulated as powders (dry seed treatment DS or water disperible powder WS) or liquids (flowable concentrate FS, liquid seed treatment LS), or microcapsule suspensions CS for use in seed treatments. The formulations can be applied to the seed by standard techniques and through conventional seed treaters. In use the compositions are applied to the nematodes, to the locus of the nematodes, to the habitat of the nematodes, or to growing plants liable to infestation by the nematodes, by any of the known means of applying pesticidal compositions, for example, by dusting, spraying, or incorporation of granules.

The compounds of the invention may be the sole active ingredient of the composition or they may be admixed with one or more additional active ingredients such as nematicides or agents which modify the behaviour of nematodes such as hatching factors, insecticides, synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect or overcoming repellency. Additionally multi-component mixtures of this type may help to overcome or prevent the development of resistance to individual components.

The particular additional active ingredient included will depend upon the intended utility of the mixture and the type of complementary action required. Examples of suitable insecticides include the following:

a) Pyrethroids such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenofos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazinon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflumuron, or chlorofluazuron;

e) Organic tin compounds such as cyhexatin, fenbutatin oxide, azocyclotin;

f) Macrolides such as avermectins or milbemycins, for example such as abamectin, avermectin, and milbemycin;

g) Hormones and pheromones;

h) Organochlorine compounds such as benzene hexachloride, DDT, endosulfan, chlordane or dieldrin;

i) Amidines, such as chlordimeform or amitraz;

j) Fumigant agents;

k) nitromethylenes such as imidacloprid.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, motilicides such as dicofol or propargite, acaricides such as bromopropylate, chlorobenzilate, or growth regulators such as hydramethylon, cyromazin, methoprene, chlorfluazuron and diflubenzuron may also be included in the compositions.

Examples of suitable synergists for use in the compositions include piperonyl butoxide, sesamax, safroxan and dodecyl imidazole.

Suitable herbicides, fungicides and plant-growth regulators for inclusion in the compositions will depend upon the intended target and the effect required.

An example of a rice selective herbicides which can be included is propanil, an example of a plant growth regulator for use in cotton is "Pix", and examples of fungicides for use in rice include blasticides such as blasticidin-S. The ratio of the compound of the invention to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

Compounds of Formula (I) according to the invention also show fungicidal activity and may be used to control one or more of a variety of plant pathogens. In a further aspect the invention therefore includes a method of combating fungi which comprises applying to a plant, to a seed of a plant or to the locus of the plant or seed a fungicidally effective amount of a compound as herein defined or a composition containing the same. The invention further includes a fungicidal composition comprising a fungicidally effective amount of a compound as herein defined and a fungicidally acceptable carrier or diluent therefor.

Examples of plant pathogens which the compounds or fungicidal compositions of the invention may control, methods by which fungi may be combatted and the form of suitable compositions, including acceptable carriers and diluents, adjuvants such as wetting, dispersing, emulsifying and suspending agents, and other ingredients, such as fertilisers and other biologically active materials, are described, for instance, in International application No WO 93/08180, the content of which is incorporated herein by reference.

The invention is illustrated by the following Examples in which percentages are by weight and the following abbreviations are used: gc=gas chromatography; nmr=nuclear magnetic resonance; s=singlet; d=doublet; t=triplet; q=quartet; m=multipier; dd=double doublet; ddt=double doublet of triplets, dtd=double triplet of doublets; b or br=broad; g=grammes; mg=milligrammes; $CDCl_3$= deuterochloroform; Chemical shifts ($\delta$) are measured in parts per million from tetramethylene silane. $CDCl_3$ was used as solvent unless otherwise stated. $M^+$=molecular ion as determined by mass spectrometry; ir=infra red spectrometry; tlc=thin layer chromatography; (dec)=decomposed on melting.

The invention is illustrated by the following Examples in which percentages are by weight and the following abbreviations are used: gc=gas chromatography; nmr=nuclear magnetic resonance; s=singlet; d=doublet; triplet; q=quartet; m=multiplet; g=grammes; mg=milligrammes; $CDCl_3$= deuterochloroform; DMSO=$d_6$-dimethyl sulphoxide; Chemical shifts ($\delta$) are measured in parts per million from tetramethylene silane. $CDCl_3$ was used as solvent unless otherwise stated. $M^+$=molecular ion as determined by mass spectrometry; ir=infra red spectrometry; tlc=thin layer chromatography.

EXAMPLE 1A

A general two step procedure for the preparation of 4-aryl-, 4-alkyl-, or 4-alkoxyalkyl-2-pyrimidinethiones from the corresponding methyl ketone is illustrated by the following preparation of 4-(dimethoxymethyl)-2(1H)-pyrimidinethione from 1,1-dimethoxyacetone. A review of this chemistry is given by R. F. Abdulla and R. S. Brinkmeyer in Tetrahedron 35, 1675 (1979).

Step 1: 4-dimethylamino-1,1-dimethoxy-3-buten-2-one 1,1-dimethoxyacetone (pyruvic aldehyde dimethyl acetal, Aldrich Chemical Co.) (3 $cm^3$) was added dropwise with stirring to tert-butoxy-bis(dimethylamino)methane (Fluka Chemie AG) (5 $cm^3$) and stirring continued at ambient temperature for 16 hours. The low-boiling impurities were removed by evaporation under reduced pressure. This left an orange oil (5.82 g) ($^1$H NMR ($CDCl_3$): $\delta$2.88(3H,br s); 3.10(3H,br s); 3.40(6H,s); 4.58(1H,s); 5.34(1H,d); 7.76(1H, d)).

Step 2: 4-(dimethoxymethyl)-2(1H)-pyrimidinethione

The product from step 1 (4.8 g), thiourea (2.53 g) and potassium methylate (2.33 g) were heated together in boiling propan-2-ol (30 cm³) for 6 hours. The reaction mixture was allowed to cool overnight. The solvent was removed by evaporation under reduced pressure, the residue was dissolved in water and washed with ethyl acetate, the organic layer being discarded. The basic aqueous layer was acidified to pH 5 using glacial acetic acid and the product was extracted into ethyl acetate. Evaporation of the ethyl acetate under reduced pressure gave 3.769 g of an orange oil. $^1$H NMR (DMSO): δ3.46(6H,s); 5.14(1H,s); 6.94(1H,d); 7.18 (1H,br s); 8.18(1H,d).

The following intermediate compounds were prepared according to the two-step procedure of Example 1A. The starting materials were commercially available.

(i) 4-phenyl-2(1H)-pyrimidinethione. $^1$H NMR (DMSO): δ3.5(1H, br s); 7.58(1H,d); 7.60–7.78(3H,m); 8.24(1H,d); 8.30(2H,dd) (yellow solid).

(ii) 4-[3-(trifluoromethyl)phenyl]-2(1H)-pyrimidinethione. $^1$H NMR (DMSO): δ7.70(1H,t); 7.86(1H, d) 8.08(1H,d); 8.24(1H,s); 8.38(1H,d); 8.84(1H,d) (orange solid).

(iii) 4-(4-fluorophenyl)-2(1H)-pyrimidinethione. $^1$H NMR (DMSO): δ7.44–7.54(2H,m); 7.56(1H,d); 8.20(1H,d) 8.30–8.40(2H,m); 13.90(1H,br s) (yellow solid).

(iv) 4-(4-nitrophenyl)-2(1H)-pyrimidinethione. $^1$H NMR (DMSO): δ7.56(1H,d); 8.20(1H,d); 8.30–8.44(4H,m) (orange-brown solid).

(v) 4-cyclopropyl-2(1H)-pyrimidinethione. $^1$H NMR (DMSO): δ1.12–1.28(4H,m); 2.12–2.24(1H,m); 6.90(1H,d); 7.98(1H,d) (orange solid).

(vi) 4-(1-methylcyclopropyl)-2(1H)-pyrimidinethione. $^1$H NMR (DMSO): δ1.00–1.08(2H,m); 1.30–1.38(2H, m); 1.48(3H,s); 6.84(1H,d); 7.92(1H,d); 13.54(1H,br s) (yellow solid).

The following pyrimidine intermediate compound was prepared according to an analogous procedure to that of Example 1A, step 2, starting from ethyl 2-formylpropionate.

(vii) 2-mercapto-5-methyl-4(3H)-pyrimidinone $^1$H NMR (DMSO): δ1.86(3H,s); 7.40(1H,s); 12.24(1H,br s); 12.48 (1H,br s).

EXAMPLE 1B

A general two step procedure for the preparation of 6-alkoxyl-4(3H)-pyrimidinethiones from 4,6-dichloropyrimidine is illustrated by the following preparation of 6-(2,2,2-trifluoroethoxy)-4(3H)-pyrimidinethione.

Step 1: 4-chloro-6-(2,2,2-trifluoroethoxy)-pyrimidine 4,6-dichloropyrimidine (20 g) potassium carbonate (37 g) and 2,2,2-trifluoroethanol (10.3 cm³) were stirred together at ambient temperature in dry dimethyl formamide (DMF) (130 cm³) for seven hours. The mixture was stored at ambient temperature for 60 hours before being poured into water. The product was extracted with diethyl ether and the organic layer was washed with saturated brine and dried over magnesium sulfate. Evaporation under reduced pressure afforded 4-chloro-6-(2,2,2-trifluoroethoxy)-pyrimidine as a 1:1.5 mixture with residual DMF. $^1$H NMR (CDCl₃): δ4.79–4.89(2H,q); 6.93(1H, s); 8.61(1H,s). This was used directly in step 2.

Step 2: 6-(2,2,2-trifluoroethoxy)-4(3H)-pyrimidinethione

The product from step 1 (14.26 g in DMF) and sodium hydrosulfide dihydrate (6.17 g) were combined in ethanol (100 cm³) and the mixture heated under reflux for four hours. The reaction was cooled, allowed to stand for 40 hours, then added to water and the product extracted into ethyl acetate. The organic layer was washed with saturated brine and dried over magnesium sulfate. Evaporation under reduced pressure afforded crude product as an oily orange solid. This was dissolved in 2M aqueous sodium hydroxide and the basic aqueous layer was washed with ethyl acetate. The organic layer was discarded. The remaining aqueous layer was acidified with concentrated hydrochloric acid, and a white product precipitated. This was recovered by filtration and air dried to give an off-white solid (9 g) $^1$H NMR (CDCl₃): δ4.8(2H,q); 6.9(1H,s); 8.1(1H,s).

The following 4-alkoxy-2(1H)-pyrimidinethione intermediate compounds were prepared according to a two-step procedure analogous to that of Example 1B, starting from 2,4-dichloropyrimidine.

(i) 4-(prop-2-yloxy)-2(1H)-pyrimidinethione. $^1$H NMR (CDCl₃): δ1.36(6H,d); 5.66(1H,septet); 6.18(1H,d); 7.54 (1H,d).

(ii) 4-(2,2,2-trifluoroethoxy)-2(1H)-pyrimidinethione. $^1$H NMR (CDCl₃): δ4.84(2H,q); 6.28(1H,d); 7.58(1H,d); 13.40 (1H, br s).

(iii) 4-ethoxy-2(1H)-pyrimidinethione. $^1$H NMR (CDCl₃): δ1.38(3H,t); 4.50(2H,q); 6.14(1H,d); 7.48(1H,d).

The following 2(1H)-pyrimidinethione intermediate compounds were prepared according to a procedure analogous to that of Example 1B, step 2, starting from known chloropyrimidines.

(iv) 2-mercapto-4-pyrimidinecarboxamide. $^1$H NMR (DMSO): δ3.48(1H,s); 7.94(1H,d); 8.18(1H,br s); 8.22(1H, br s); 9.06(1H,d).

(v) 5-nitro-2,4(1H,3H)-pyrimidinedithione. $^1$H NMR (DMSO): δ8.80(1H,s); 13.08(1H,br s); 13.32(1H,br s).

(vi) 5-nitro-2(1H)-pyrimidinethione.

(vii) 2-methylthio-4(3H)-pyrimidinethione.

(viii) 4(1H)-quinazolinethione

EXAMPLE 1C

Pyrimidinethione intermediates are alternatively prepared from the corresponding halo or per-halo pyrimidines by displacement of the halogen(s) using thiourea, as illustrated for the preparation of 6-mercapto-4(1H)-pyrimidinethione.

4,6-dichloropyrimidine (2.5 g), thiourea (1.27 g) and propan-2-ol (30 cm³) were stirred and heated under reflux for 4 hours. The reaction was cooled in ice and the precipitate filtered off and dried. The orange solid (1.751 g) was dissolved in 2M aqueous sodium hydroxide (20 cm³) and left to stand for 18 hours. The solution was acidified to pH 1 with concentrated hydrochloric acid, and the mixture cooled in a refrigerator for 3 hours. The product was filtered off, washed with cold water and dried by azeotroping with acetone, giving 6-mercapto-4(1H)-pyrimidinethione (1.204 g). $^1$H NMR (DMSO): δ7.58(1H,s); 8.42(1H,s); 14.36(1H,br s); 14.54(1H,br s).

EXAMPLE 1D

The standard synthesis (see D. J. Brown, "The Pyrimidines", Wiley 1962) for the preparation of 4-alkyl, and 4-(substituted alkyl) 6-hydroxy-2(1H)-pyrimidinethiones from beta-keto esters and thiourea or S-substituted thioureas was used to prepare these intermediates, as illustrated by the following preparation of 2,3-dihydro-2-thioxo-6-(trifluoromethyl)-4(1H)-pyrimidinone.

Thiourea (1 g) and potassium carbonate (4.5 g) were heated under reflux in propan-2-ol (30 cm³) for 30 minutes.

Ethyl trifluoroacetoacetate (2 cm³) was added and heating continued for seven hours. The reaction mixture was cooled and acidified to pH 6 with concentrated hydrochloric acid (effervescence). Further 2M aqueous hydrochloric acid (50 cm³) was added and the precipitate was recovered by filtration, washed with water and dried by azeotroping with acetone to give a white solid (0.657 g). $^1$H NMR (DMSO): δ6.48(1H,s); 12.92(1H,br s); 13.6 (1H,broad)

EXAMPLE 1E

This example illustrates the two-step preparation of 2-mercapto-4-pentafluoroethylpyrimidine.

Step 1: 4-(pentafluoroethyl)-2(1H)-pyrimidinone

Pentafluoropropionic anhydride (62 g) was cooled in an ice-bath to 5° C. and pyridine (15.8 g) was added dropwise with stirring. The temperature was maintained between 10°–15° C. while ethyl vinyl ether (14.4 g) in pyridine (15.8 g) was added dropwise over 40 minutes. This gave a thick pale yellow gum which was stirred for a further 1 hour at 20° C. and then 25 cm³ of water was added (exotherm)., resulting in an orange clear solution. Urea (12 g) in ethanol (40 cm³) and water (20 cm³) was added and the resulting mixture was heated under reflux for 3 hours. The reaction was cooled to 5° C. and stirred for 30 minutes. The precipitate that formed was recovered by filtration and washed with water and hexane, to give a pale orange solid which was dried in a vacuum dessicator (18 g). M$^+$=214.

Step 2: 4-(pentafluoroethyl)-2(1H)-pyrimidinethione

The product from step 1 (2 g) was dissolved in phosphorus oxychloride (5 cm³) and heated under reflux for 3 hours. Excess reagent was removed by evaporation under reduced pressure and the residue azeotroped with toluene to remove last traces of the phosphorus oxychloride. The residue was dissolved in dry dimethylformamide (15 cm³) and sodium hydrosulfide dihydrate (1.75 g) added. The mixture was stirred for 3 hours and then left standing for 72 hours. The reaction mixture was poured into water and the resulting precipitate was filtered off and discarded. The aqueous filtrate was acidified to pH 1 with 2M hydrochloric acid and the product extracted into ethyl acetate. The organic layer was evaporated under reduced pressure to give a brown oil which was dissolved in 2M aqueous sodium hydroxide (15 cm³) and washed with dichloromethane twice to remove DMF residues. The aqueous layer was acidified to pH 1 with c. hydrochloric acid and the resulting precipitate of product was recovered by filtration, washing with water. The mustard-coloured solid was dried by azeotroping with acetone and gave 0.424 g.

EXAMPLE 2

The preparation of compounds according to the invention, by Wittig condensation of a 3-oxopropylthio-substituted pyrimidine with dibromodifluoromethane in the presence of triphenyl phosphine, is illustrated by the following 3-step preparation of Compound No. 1.

Step 1: 2-[2-(1,3-dioxolan-2-yl)ethylthio]-pyrimidine

Potassium carbonate (0.766 g) was added to a stirred solution of 2-mercaptopyrimidine (0.622 g) in acetone (10 cm³) at ambient temperature. 2-(2-Bromoethyl)-1,3-dioxolane (1 g) was added to the resulting mixture and the reaction heated under reflux for 3.5 hours. The reaction mixture was left to cool overnight, then poured into water and extracted with diethyl ether. The organic phase was dried with magnesium sulfate and evaporated under reduced pressure to give a yellow oil. This material was used in step 2 without further purification. M$^+$=212; $^1$H NMR (CDCl₃): δ2.25 (2H,m); 3.25(2H,t); 3.90 (2H,m); 4.00 (2H,m); 5.05 (1H,t); 6.96 (1H,t); 8.52 (2H,d).

Step 2: 2-(3-oxopropylthio)-pyrimidine

Aqueous 10% hydrochloric acid (20 cm³) was added to a solution of 2-(2-(1,3-dixolan-2-yl)-ethylthio)-pyrimidine (2 g) in tetrahydrofuran (20 cm³) and the mixture stirred at ambient temperature for 30 hours. The mixture was poured into water, neutralised to pH7, and the precipitated orange gum extracted with ethyl acetate. The organic phase was dried with magnesium sulfate and evaporated under reduced pressure to give an orange oil which was chromatographed on silica gel using 3:7 ethyl acetate:hexane as eluant to give 2-(3-oxopropylthio)-pyrimidine as a yellow gum. M$^+$=168; $^1$H NMR (CDCl₃): δ2.99 (2H,t); 3.40 (2H,t); 6.98 (1H,t); 8.50 (2H,d); 9.84 (1H,s)

Step 3: 2-[4,4-difluoro-3-butenyl)thio]-pyrimidine (Compound No. 1)

A dry reaction flask was purged with nitrogen and charged with a solution of 2-(3-oxopropylthio)-pyrimidine (0.176 g) and dibromodifluoromethane (0.44 g) in dry dimethylacetamide (4.5cm³). The stirred solution was cooled to 0° C. After 10 minutes triphenylphosphine (0.549 g) was added and the reaction stirred at 0° C. for an additional 30 minutes before allowing the reaction to warm to the ambient temperature. Zinc dust (0.136 g) was added in portions and the mixture then heated at 90° C. for 2 hours, cooled, and stood at the ambient temperature for 8 days. The reaction mixture was filtered through a plug of High-Flo filter aid and the solid residues rinsed with ethyl acetate. The filtrate and washings were combined and washed with water. The organic phase was dried with magnesium sulfate and evaporated under reduced pressure to give an oily-solid residue which was subjected to column chromatography on silica gel, eluting with 1:4 tert-butylmethylether: hexane to give Compound No. 1 as a pale yellow oil. M$^+$=202; $^1$H NMR (CDCl₃): δ2.45(2H,m); 3.19(2H,t); 4.30(1H,m); 6.99(1H,t); 8.52(2H, d).

Compound 1 may also be prepared by the method of EXAMPLE 4B.

EXAMPLE 3A

This Example illustrates the preparation of 1,4-dibromo-1,1,2-trifluorobutane.

A solution of 4-bromo-1,1,2-trifluoro-1-butene (Fluorochem Ltd.) (2.5 g) in dry dichloromethane (25 cm³) at 0° C. was treated with hydrogen bromide gas for 45 minutes. The reaction mixture was then stirred at 0° C. for 1 hour. The reaction mixture was made alkaline with 5% sodium bicarbonate solution and extracted twice with dichloromethane. The combined dichloromethane extracts were dried over magnesium sulfate, filtered and concentrated under reduced pressure to give a pale yellow liquid (2.84 g). The material was shown by gc analysis to be greater than 99% pure. $^1$H NMR (CDCl₃): δ2.15–2.59(2H,m); 3.42–3.69(2H,m); 4.75–5.07(1H,m).

EXAMPLE 3B

This Example illustrates the two step process for the preparation of the 4,4-difluoro-3-butenyl ester of 4-methyl-benzenesulfonic acid.

Step 1: 4-bromo-3,4,4-trifluorobutyl 4-methyl-benzenesulfonate

The product from Example 3A (1 g) was added dropwise to a stirred suspension of silver tosylate (1.03 g) in acetonitrile (10 cm³) at ambient temperature, protected from the light. The reaction was then heated under reflux for 24 hours after which gc analysis indicated complete consumption of starting material. The reaction mixture was cooled to the ambient temperature and the precipitate was filtered off and washed with ethyl acetate. The filtrate and ethyl acetate washings were combined and washed with water and the aqueous layer extracted with ethyl acetate. The combined ethyl acetate layers were washed with water and brine, dried over magnesium sulfate and evaporated under reduced pressure to give a brown oil (1.21 g). GC analysis showed this material to be >99% pure. ¹H NMR (CDCl₃): δ2.20(2H,m); 2.46(3H,s); 4.19(2H,m); 4.74(1H,m); 7.38(2H,d); 7.80(2H, d).

Step 2: 4,4-difluoro-3-butenyl 4-methyl-benzenesulfonate

To a stirred suspension of powdered zinc (1.41 g) and iodine (one grain, catalytic) in methanol (3 cm³) was added a solution of 4-bromo-3,4,4-difluorobutyl p-tolylsulfonate (0.71 g) in methanol (2 cm³). The reaction mixture was heated under reflux for 2½ hours after which gc analysis indicated complete consumption of starting material. The organic phase was pipetted from the zinc suspension and the zinc was washed with 3 portions of ethyl acetate. The combined ethyl acetate portions were washed with 2M hydrochloric acid, dried over magnesium sulfate and evaporated under reduced pressure to give a brown liquid (0.47 g). GC analysis showed this material to be >99% pure. ¹H NMR (CDCl₃): δ2.35(2H,m); 2.46(3H,s); 4.01(2H,m); 4.15(1H, m); 7.38(2H,d); 7.79(2H,d).

EXAMPLE 3C

This Example illustrates the three step preparation of 4-bromo-4,4-difluorobutyl methanesulfonate.

Step 1: 4-bromo-4,4-difluorobutanoic acid.

To a stirred solution of acrylic acid (1.44 g) and acetonitrile (80 cm³) was added sodium dithionite (4.18 g), sodium bicarbonate (2.01 g), water (20 cm³) and finally dibromodifluoromethane (5 cm³). The biphasic mixture was stirred at the ambient temperature with the inorganic salts gradually dissolving. GC analysis after 4 hours indicated complete consumption of acrylic acid. The aqueous phase was saturated with solid sodium chloride. The organic phase was separated, dried over magnesium sulfate, filtered and evaporated under reduced pressure to give a pale yellow oil with a small amount of a white solid. This mixture was taken up in ethyl acetate, filtered and solvent evaporated under reduced pressure to give a pale yellow oil (2.54 g). ¹H NMR (DMSO): δ2.45(2H,t); 2.65(2H,m).

Step 2: 4-bromo-4,4-difluorobutanol.

Under an atmosphere of nitrogen a solution of lithium aluminium hydride in diethylether (5 cm³, 5 mM) was cooled to 0° C. Maintaining this temperature 4-bromo-4,4-difluorobutanoic acid (1 g) dissolved in dry diethylether (5 cm³) was added dropwise with stirring. After an hour at 0° C. the reaction mixture was cautiously quenched by the addition of 2M hydrochloric acid. The organic phase was separated, washed with saturated sodium bicarbonate solution, dried over magnesium sulfate, filtered and evaporated under reduced pressure to give a colourless oil (0.57 g). ¹H NMR (CDCl₃): δ1.82-1.96(2H,m); 2.40-2.60 (2H,m); 3.74(2H,t).

Step 3: 4-bromo-4,4-difluorobutyl methanesulfonate.

A stirred solution of 4-bromo-4,4-difluorobutanol (0.57 g) in dry diethylether (5 cm³) was cooled to 0° C. Maintaining this temperature, triethylamine (1.7 cm³) was added. After ten minutes methanesulfonyl chloride (0.3 cm³) was added and the mixture stirred for a further hour at 0° C. The reaction mixture was poured into 2M hydrochloric acid (2 cm³) and diethylether (20 cm³). The organic phase was separated, washed with saturated brine, then passed through a plug of silica gel eluting with further diethylether. The diethylether fractions were evaporated under reduced pressure to give a light yellow oil (0.705 g). ¹H NMR (CDCl₃): δ2.04–2.18(2H,m); 2.46–2.64(2H,m); 3.04(3H,s); 4.32(2H, t).

EXAMPLE 3D

This example illustrates the preparation of 4,4-difluoro-3-butenyl-thiourea (as its 4-methyl-benzenesulfonate salt), which is an intermediate of general use in the preparation of compounds according to the invention directly by standard pyrimidine syntheses in which it can replace, for example, methyl-thiourea.

Thiourea (0.29 g) and 4,4-difluoro-3-butenyl 4-methyl-benzenesulfonate (see Example 3B) (1 g) were heated together under reflux in ethanol (20 cm³) for 24 hours. The reaction mixture was cooled and the solvent evaporated under reduced pressure to give an oil which slowly crystallised. Trituration with hexane gave (4,4-difluoro-3-butenyl)-thiourea tosylate salt (1.14 g). MH⁺(FAB)=167; ¹H NMR (DMSO): 2.48(3H,s); 2.46–2.58(2H,m); 3.42(2H,t); 4.66–4.84(1H,m) 7.32(2H,d); 7.68(2H,d); 9.10–9.40(3H, broad)

EXAMPLE 4A

A general procedure for the two-step preparation of pyrimidines substituted with a 4,4-difluoro-3-butenylthio group in the 2, 4 or 5-position, is by reaction of the corresponding substituted mercaptopyrimidine with 1,4-dibromo-4,4-difluorobutyl methanesulfonate (see Example 3C), followed by dehydrohalogenation of the product obtained. This is illustrated by the following preparation of Compound No. 5

Step 1: 4-[(4-bromo-4,4-difluorobutyl)thio]-pyrimidine

A mixture of 4-bromo-4,4-difluorobutyl methanesulfonate (2.4 g), 4(3H)-pyrimidinethione (1.1 g), potassium carbonate (5 g) and acetone (60 cm³) was stirred at ambient temperature for 18 hours. Inorganic solids were removed by filtration and the filtrate evaporated under reduced pressure to give a brown oil (2.785 g). Chromatography on silica gel using 1:4 ethyl acetate:hexane as eluant gave a light yellow oil (1.536 g). ¹H NMR (CDCl₃): δ2.02–2.14(2H,m); 2.46–2.62(2H,m); 3.30(2H,t); 7.18(1H,d); 8.35(1H,d); 8.94 (1H,s).

Step 2: 4-[(4,4-difluoro-3-butenyl)thio]-pyrimidine (Compound No. 5)

1,8-Diazabicyclo[5.4.0]undec-7-ene (DBU) (0.75 cm³) was added dropwise to a stirred solution of the product from step 1 (1.4 g) in dry diethyl ether (20 cm³). After two hours at ambient temperature, the reaction mixture was heated under reflux for two hours. Further DBU (0.75 cm³) was added and the reaction refluxed for another three hours then left to cool overnight. The mixture was poured into water (20 cm³) and the organic phase separated. The aqueous phase was extracted with ethyl acetate (25 cm³). The combined organic phases were washed with saturated ammonium chloride solution (20 cm³), dried over anhydrous magnesium sulfate, filtered and evaporated under reduced pressure to give an orange oil (0.98 g). Chromatography on silica gel using 1:4 ethyl acetate: hexane as eluant gave Compound No. 5 (0.868 g). M$^+$202; $^1$H NMR (CDCl$_3$): δ2.35–2.48(2H, m); 3.26(2H,t); 4.18–4.36(1H,m); 7.18(1H,d); 8.34(1H,d); 8.94(1H,s); (oil).

Compound No. 29 according to the invention and the corresponding intermediate compound were prepared according to the two-step procedure of Example 4A:

(i) 2-[(4,4-difluoro-3-butenyl)thio]-4-methylpyrimidine (Compound No. 29). M$^+$=216; $^1$H NMR (CDCl$_3$): δ2.38–2.52(2H,m); 2.45(3H,s); 3.2(2H,t); 4.2–4.4(1H, m); 6.83(1H,d); 8.35(1H,d) (oil), from 4-methyl-2(1H)-pyrimidinethione via 2-[(4-bromo-4,4-difluorobutyl)thio]-4-methylpyrimidine ($^1$H NMR (CDCl$_3$): δ2.1(2H, m); 2.4–2.6(2H,m); 2.45(3H,s); 3.2(2H,t); 6.83(1H,d); 8.35(1H,d) (oil)).

EXAMPLE 4B

A general one-step procedure for the preparation of pyrimidines substituted with a 4,4-difluoro-3-butenylthio group in the 2, 4 or 5-position, starting with a correspondingly substituted mercaptopyrimidine, is illustrated by the following preparation of 2-[(4,4-difluoro-3-butenyl)thio]-4-phenyl-pyrimidine (Compound No. 4) from 4-phenyl-2(1H)-pyrimidinethione (see Example 1(i)) and 4,4-difluoro-3-butenyl 4-methyl-benzenesulfonate (see Example 3B).

4-Phenyl-2(1H)-pyrimidinethione (0.29 g), 4,4-difluoro-3-butenyl 4-methyl-benzenesulfonate (0.4 g), potassium carbonate (0.22 g) and potassium iodide (catalytic amount) were mixed in acetone (20 cm$^3$) and heated under reflux for five hours then allowed to cool overnight. The precipitate formed was removed by filtration and the filtrate evaporated under reduced pressure to give an orange solid. Chromatography on silica gel using a 90:10 mixture of hexane:ethyl acetate as eluant gave Compound No. 4 as a yellow oil (0.253 g). M$^+$=278; $^1$H NMR (CDCl$_3$): δ2.48–2.58(2H,m); 3.28(2H,t); 4.24–4.42(1H,m); 7.38(1H,d); 7.48–7.56(3H, m); 8.04–8.12(2H,m); 8.56(1H,d).

The following compounds according to the invention were prepared using the procedure of Example 4B. Where the mercaptopyrimidines are not readily available commercially, they may be prepared by the procedures of Examples 1, or by methods analogous to these.

(i) 2-[(4,4-difluoro-3-butenyl)thio]-4-(dimethoxymethyl)-pyrimidine (Compound No. 62). M$^+$=276; $^1$H NMR (CDCl$_3$): δ2.38–2.50(2H,m); 3.20(2H,t); 3.42(6H,s); 4.20–4.38(1H,m); 5.18(1H,s); 7.20(1H,d); 8.56(1H,d); (oil) (see Example 1A for preparation of starting material).

(ii) 2-[(4,4-difluoro-3-butenyl)thio]-4-[3-(trifluoromethyl)phenyl]-pyrimidine (Compound No. 76). M$^+$=346; $^1$H NMR (CDCl$_3$): δ2.44–2.58(2H,m); 3.26(2H,t); 4.24–4.42(1H,m); 7.42(1H,d); 7.64(1H,t); 7.78(1H,d); 8.26(1H,d); 8.34(1H,s); 8.62(1H,d); (oil) (see Example 1A (ii) for preparation of starting material).

(iii) 2-[(4,4-difluoro-3-butenyl)thio]-4-(4-fluorophenyl)-pyrimidine (Compound No. 43). M$^+$=296; $^1$H NMR (CDCl$_3$): δ2.46–2.58(2H,m); 3.26(2H,t); 4.24–4.42(1H,m); 7.14–7.24(2H,m); 7.34(1H,d); 8.04–8.14(2H,m); 8.54(1H, d); (off-white solid mp 44°–45° C.) (see Example 1A (iii) for preparation of starting material).

(iv) 2-[(4,4-difluoro-3-butenyl)thio]-4-(4-nitrophenyl)-pyrimidine (Compound No. 77). M$^+$=323; $^1$H NMR (CDCl$_3$): δ2.46–2.58(2H,m); 3.28(2H,t); 4.24–4.42(1H,m); 7.46(1H,d); 8.24(2H,d); 8.38(2H,d); 8.68(1H,d); (orange-yellow solid mp 88.5°–89.5° C.) (see Example 1A (iv) for preparation of starting material).

(v) 4-cyclopropyl-2-[(4,4-difluoro-3-butenyl)thio]-pyrimidine (Compound No. 46). M$^+$=242; $^1$H NMR (CDCl$_3$): δ1.02–1.20(4H,m); 1.84–1.98(1H,m); 2.34–2.48(2H,m); 3.10(2H,t); 4.18–4.38(1H,m); 6.82(1H,d); 8.26(1H, d); (oil) (see Example 1A (v) for preparation of starting material).

(vi) 2-[(4,4-difluoro-3-butenyl)thio]-4-(1-methylcyclopropyl)-pyrimidine (Compound No. 47). M$^+$=256; $^1$H NMR (CDCl$_3$): δ0.88–0.94(2H,m); 1.32–1.38 (2H,m); 1.48(3H,s); 2.36–2.48(2H,m); 3.10(2H,t); 4.20–4.38(1H,m); 6.94(1H,d); 8.34(1H,d); (oil) (see Example 1A (vi) for preparation of starting material).

(vii) 2-[(4,4-difluoro-3-butenyl)thio]-4-pentafluoroethylpyrimidine (Compound No. 61). M$^+$=320; $^1$H NMR (CDCl$_3$): δ2.38–2.52(2H,m); 3.18(2H,t); 4.18–4.38(1H,m); 7.32(1H,d); 8.76(1H,d) (oil) (see Example 1E for preparation of starting material).

(viii) 4,5-diamino-2-[(4,4-difluoro-3-butenyl)thio]-pyrimidine (Compound No. 64). M$^+$=232; $^1$H NMR (CDCl$_3$): δ2.41(2H,m); 2.88–2.95(2H,br s); 3.10(2H,t); 4.2–4.4(1H,m); 4.78–4.88(2H,br s); 7.73(1H,s); (beige solid mp 83°–84° C.).

(ix) 4-[(4,4-difluoro-3-butenyl)oxy]-2-[(4,4-difluoro-3-butenyl)thio]-6-(trifluoromethyl)-pyrimidine (Compound No. 68). $^1$H NMR (CDCl$_3$): δ2.38–2.54(4H,m); 3.18(2H,t); 4.18–4.38(2H,m); 4.40(2H,t); 6.72(1H,s) (oil) (see Example 1D for preparation of starting material).

(x) 2-[(4,4-difluoro-3-butenyl)thio]-5-methyl-4(3H)-pyrimidinone (Compound No. 71). $^1$H NMR (CDCl$_3$): δ2.04 (3H,s); 2.36–2.48(2H,m); 3.20(2H,t); 4.18–4.36(1H,m); 7.72(1H,s); 12.22(1H,br s) (off-white solid mp 100°–100.5° C.) (see Example 1A (vii) for preparation of starting material).

(xi) 2-[(4,4-difluoro-3-butenyl)thio]-6-trifluoromethyl-4(3H)-pyrimidinone (Compound No. 72). $^1$H NMR (CDCl$_3$): δ2.40–2.52(2H,m); 3.28(2H,t); 4.18–4.36(1H,m); 6.60(1H, s) (white solid, mp 83°–84.5° C.) (see Example 1D for preparation of starting material).

(xii) 2-[(4,4-difluoro-3-butenyl)thio]-4-ethoxy-6-phenylpyrimidine (Compound No. 75). M$^+$=322; $^1$H NMR (CDCl$_3$): δ1.41(3H,t); 2.52(2H,m); 3.22(2H,t); 4.22–4.42(1H,m); 4.45(2H,q); 6.79(1H,s); 7.49(3H,m); 8.01(2H,m) (oil).

(xiii) 4-[(4,4-difluoro-3-butenyl)thio]-2-(methylthio)-pyrimidine (Compound No. 78). M$^+$=248; $^1$H NMR (CDCl$_3$): δ2.42(2H,m); 2.52(3H,s); 3.21(2H,t); 4.18–4.35 (1H,m); 6.80(1H,d); 8.10(1H,d) (oil) (see Example 1B (vii) for preparation of starting material).

(xiv) 2-[(4,4-difluoro-3-butenyl)thio]-5-nitropyrimidine (Compound No. 84). M$^+$=247; $^1$H NMR (CDCl$_3$): δ2.42–2.54(2H,m); 3.28(2H t); 4.2–4.38(1H,m); 9.26(2H,s) (oil) (see Example 1B (vi) for preparation of starting material).

(xv) 2,4-bis-[(4,4-difluoro-3-butenyl)thio]-5-nitropyrimidine (Compound No. 94). M$^+$=369; $^1$H NMR (CDCl$_3$): δ2.38–2.52(4H,m); 3.20–3.30(4H,m); 4.18–4.38 (2H,m); 9.12(1H,s) (oil) (see Example 1B (v) for preparation of starting material).

(xvi) 4-[(4,4-difluoro-3-butenyl)thio]-quinazoline (Compound No. 95).

M$^+$=252; $^1$H NMR (CDCl$_3$): δ2.51(2H,m); 3.41(2H,t); 4.25–4.4(1H,m); 7.60(1H,t); 7.88(1H,t); 7.98(1H,d); 8.10 (1H,d); 9.00(1H,s) (oil) (see Example 1B (viii) for preparation of starting material).

EXAMPLE 4C

An alternative alkylation method to that given in Example 4B may be advantageous in cases where the starting pyrimidinethione is of low solubility in acetone. This is illustrated for the preparation of 2-[(4,4-difluoro-3-butenyl)thio]-4-pyrimidinecarboxamide, Compound No. 81.

A mixture of 4,4-difluoro-3-butenyl 4-methylbenzenesulfonate (see Example 3B) (0.85 g), sodium iodide (0.5 g) and ethanol (10 cm$^3$) was heated under reflux for ninety minutes. The resulting mixture, now containing 4,4-difluoro-1-iodo-3-butene was added to a suspension of 2-mercapto-4-pyrimidinecarboxamide (0.75 g) in 1M aqueous sodium hydroxide (5 cm$^3$) and vigorously stirred for 18 hours. The reaction was quenched into water and the product extracted into ethyl acetate. The organic layer was dried over magnesium sulfate, filtered and evaporated to give an orange solid (0.764 g). Chromatography on silica gel using dichloromethane to remove less polar impurities, then diethyl ether gave Compound No. 81 (0.629 g). M$^+$=245; $^1$H NMR (CDCl$_3$): δ2.42–2.54(2H,m); 3.22(2H,t); 4.22–4.40(1H,m); 5.86(1H,br s); 7.64(1H,br s); 7.78(1H,d); 8.78(1H,d) (mp 49°–51° C.).

The following compounds according to the invention was prepared using the procedure of Example 4C.

(i) 2-[(4,4-difluoro-3-butenyl)thio]-4(3H)-pyrimidinone (Compound No. 70). M$^+$=218; $^1$H NMR (CDCl$_3$): δ2.42 (2H,m); 3.22(2H,t); 4.15–4.35(1H,m); 6.22(1H,d); 7.88(1H,d); (white solid mp 75.5°–76.5° C.) from 2-thiouracil.

(ii) 4,6-bis-[(4,4-difluoro-3-butenyl)thio]-pyrimidine (Compound No. 98) M$^+$=324; $^1$H NMR (CDCl$_3$): δ2.34–2.46(4H,m); 3.20(4H m); 4.18–4.36(2H,m); 7.00(1H, s); 8.66(1H,s) (oil) (see Example 1C for preparation of starting material).

EXAMPLE 4D

A general procedure for the two-step preparation of pyrimidines substituted with a 4,4-difluoro-3-butenylthio group in the 2, 4 or 5-position, is by reaction of the correspondingly substituted mercaptopyrimidine with 1,4-dibromo-3,4,4-trifluorobutane, followed by dehalogenation of the product. This is illustrated by the following preparation of Compound No. 13:

Step 1: 4-[(4-bromo-3,4,4-trifluorobutyl)thio]-6-(2,2,2-trifluoroethoxy)-pyrimidine 6-(2,2,2-trifluoroethoxy)-4(3H)-pyrimidinethione (see Example 1B) (3 g) and 1,4-dibromo-3,4,4-trifluorobutane (see Example 3A) (3.86 g) were added to acetone (50 cm$^3$) containing potassium carbonate (1.97 g) and the mixture stirred at ambient temperature for 7 hours. After standing for a further 16 hours, tlc showed the reaction to be incomplete, so the mixture was heated to reflux for 5 hours. The reaction was then allowed to cool, inorganic solids were filtered off and washed with more acetone. Evaporation of the combined organic layers at reduced pressure afforded a brown oil which was chromatographed on silica gel, eluting with 1:4 ethyl acetate:hexane. This gave the title pyrimidine (3.05 g). M$^+$=399; $^1$H NMR (CDCl$_3$): δ2.2–2.4(2H,m); 3.25–3.50 (2H,m); 4.68–4.95(1H,m); 4.8(2H,q); 6.73(1H,s); 8.58(1H, s); (oil).

Step 2: 4-[(4,4-difluoro-3-butenyl)thio]-6-(2,2,2-trifluoroethoxy)-pyrimidine (Compound No. 13)

The product from step 1 (2.8 g) was treated with zinc powder (1.376 g) in methanol (100 cm$^3$) containing zinc iodide (catalytic amount). The mixture was heated under reflux for 7 hours and glc then indicated that only about 70% conversion had occurred. A further 0.459 g of zinc powder was added and heating continued for 6 hours. The cooled reaction mixture was filtered through a plug of celite, which was washed with more ethanol. The combined organic solutions were evaporated under reduced pressure to give a yellow oil. Purification by chromatography on silica gel, eluting with 1:10 ethyl acetate:hexane gave Compound No. 13 (1.1 g). M$^+$=300; $^1$H NMR (CDCl$_3$): δ2.4(2H,m); 3.2 (2H,t); 4.2–4.35(1H,m); 4.78(2H,q); 6.7(1H,s); 8.55(1H,s); (oil).

The following compounds according to the invention were prepared using the two-step method of Example 4D. Where the pyrimidinethiones are not readily available commercially, they may be prepared by the procedures of Examples 1, or by methods analogous to these.

(i) 2,4-bis-[(4,4-difluoro-3-butenyl)thio]-pyrimidine (Compound No. 36). $^1$H NMR (CDCl$_3$): δ2.15–2.45(4H,m); 3.09–3.60(4H,m); 4.64–5.00(2H,m); 6.87 (1H,d); 8.19(1H, d) from dithiouracil via 2,4-bis-[(4-bromo-3,4,4-trifluorobutyl)thio]-pyrimidine.

(ii) 2-[(4,4-difluoro-3-butenyl)thio]-4-[(4,4-difluoro-3-butenyl)oxy]-pyrimidine (Compound No. 37). $^1$H NMR (CDCl$_3$): δ2.45(4H,m); 3.19(2H,t); 4.30(2H,t); 4.35(2H,m); 6.40(1H,d); 8.21(1H,d) (oil) from 2-thiouracil via 4-[(4-bromo-3,4,4-trifluorobutyl)oxy]-2-[(4-bromo-3,4,4-trifluorobutyl)thio]-pyrimidine.

(iii) 2-[(4,4-difluoro-3-butenyl)thio]-4-(2,2,2-trifluoroethoxy)-pyrimidine (Compound No. 65) M$^+$=300; $^1$H NMR (CDCl$_3$): δ2.38–2.50(2H,m); 3.16(2H,t); 4.20–4.38(1H,m); 4.78(2H, q); 6.56(1H,d); 8.32(1H,d) (oil) (see Example 1B (ii) for preparation of starting material) via 2-[(4-bromo-3,4,4-trifluorobutyl)thio]-4-(2,2,2-trifluoroethoxy)-pyrimidine $^1$H NMR (CDCl$_3$): δ2.24–2.44 (2H,m); 3.12–3.26(1H,m); 3.40–3.52(1H,m); 4.78(2q); 4.68–4.98(1H,m); 6.58(1H,d); 8.34(1H,d).

(iv) 2-[(4,4-difluoro-3-butenyl)thio]-4-ethoxypyrimidine (Compound No. 69) $^1$H NMR (CDCl$_3$): δ1.38(3H,t); 2.40–2.50(2H,m); 3.16(2H,t); 4.20–4.38(1H,m); 4.42(2H, q); 6.38(1H,d); 8.20(1H,d) (oil), (see Example 1B (iii) for preparation of starting material) via 2-[(4-bromo-3,4,4-trifluorobutyl)thio]-4-ethoxypyrimidine $^1$H NMR (CDCl$_3$): δ1.40(3H,t); 2.24–2.48(2H,m); 3.10–3.22(1H,m); 3.40–3.50 (1H,m); 4.42(2H,q); 4.70–4.98(1H,m); 6.40(1H,d); 8.22 (1H,d).

(v) 2-[(4,4-difluoro-3-butenyl)thio]-4-(prop-2-yloxy)-pyrimidine (Compound No. 73) $^1$H NMR (CDCl$_3$): δ1.36 (6H,d); 2.38–2.50(2H,m); 3.14(2H,t); 4.20–4.38(1H,m); 5.38(1H,sept); 6.34(1H,d); 8.18(1H,d) (oil), (see Example 1B (i) for preparation of starting material) via 2-[(4-bromo-3,4,4-trifluorobutyl)thio]-4-(prop-2-yloxy)-pyrimidine $^1$H NMR (CDCl$_3$): δ1.36(6H,d); 2.20–2.46(2H,m); 3.08–3.20 (1H,m); 3.38–3.50(1H,m); 4.70–4.98(1H,m); 5.32–5.44(1H, m); 6.36(1H,d); 8.20(1H,d).

EXAMPLES 5

Procedures suitable for the preparation of compounds according to the invention by transformation or further reaction of the substituents of other compounds according to the invention are illustrated by Examples 5A to 5L.

EXAMPLE 5A

A procedure suitable for the preparation of compounds according to the invention carrying an alkoxy, or substituted alkoxy, group on the pyrimidine ring from a pre-formed hydroxy-substituted pyrimidine (or its pyrimidinone tautomer) such as Compound No. 70 is illustrated by the following procedure for the preparation of 4-benzyloxy-2-[(4,4-difluoro-3-butenyl)thio]-pyrimidine (Compound No. 16)

2-[(4,4-difluoro-3-butenyl)thio]-4(3H)-pyrimidinone (Compound 70, see Example 4C (i)) (0.2 g), benzyl bromide (0.157 g) and silver carbonate (0.253 g) were stirred and heated under reflux in toluene (20 cm$^3$) for 3 hours. The reaction mixture was cooled and filtered through celite to remove silver salts. The inorganic material was washed with acetone and the combined organic solutions were evaporated under reduced pressure to give a brown oil which was chromatographed on silica gel, eluting with 1:4 ethyl acetate:hexane. This gave 0.2 g Compound No. 16. M$^+$=308; $^1$H NMR (CDCl$_3$): δ2.43(2H,m); 3.15(2H,t); 4.20–4.38(1H, m); 5.4(2H,s); 6.48(1H,d); 7.3–7.45(5H,m); 8.22(1H,d) (oil).

The following compounds were prepared by alkylation of hydroxypyrimidines by the procedure of Example 5A (i) 2-[(4,4-difluoro-3-butenyl)thio]-4-methoxy-6-trifluoromethyl-pyrimidine (Compound No. 3) from Compound No. 72 (see Example 4B (xi)) and methyl iodide. $^1$H NMR (CDCl$_3$): δ2.40–2.54(2H,m); 3.18(2H,t); 4.02(3H,s); 4.20–4.38(1H,m); 6.72(1H,s) (oil).

(ii) 2-[(4,4-difluoro-3-butenyl)thio]-4-[(2-propenyl)oxy]-pyrimidine (Compound No. 67) from Compound No. 70 (see Example 4C (i)) and allyl bromide. M$^+$=258; $^1$H NMR (CDCl$_3$): δ2.45(2H,m); 3.15(2H,t); 4.2–4.4(1H,m); 4.89 (2H,d); 5.25–5.45(2H,m); 5.99–6.11(1H,m); 6.41(1H,d); 8.21(1H,d) (oil).

(iii) 2-[(4,4-difluoro-3-butenyl)thio]-4-methoxypyrimidine (Compound No. 93) from Compound No. 70 (see Example 4C (i)) and methyl iodide. M$^+$=232; $^1$NMR (CDCl$_3$): δ2.45(2H,m); 3.15(2H,t); 4.20–4.40(1H, m); 3.96(3H,s); 6.40(1H,d); 8.21(1H,d)

EXAMPLE 5B

A procedure suitable for the preparation of compounds according to the invention carrying an alkoxy, or substituted alkoxy, group on the pyrimidine ring from a pre-formed chloro-substituted pyrimidine such as Compound No. 63 is illustrated by the following procedure for the preparation of Compound No. 74.

Step 1: Preparation of 4-chloro-2-[(4,4-difluoro-3-butenyl)thio]-pyrimidine (Compound No. 63).

Compound No. 70 (see Example 4C (i)) (0.2 g) was stirred with phosphorus oxychloride (0.43 cm$^3$) and dichloromethane (2 cm$^3$) while being cooled in an ice/salt bath to 0° C. Triethylamine (0.14 cm$^3$) was added dropwise, taking care not to allow the internal temperature to exceed 5° C. After the addition was complete, the mixture was stirred at 0° C. for 1 hour and at ambient temperature for 90 minutes before being warmed to reflux for 3 hours. After cooling, the solvent was removed by evaporation under reduced pressure and last traces of phosphorus-containing materials were removed by azetroping with toluene. The brown oil which resulted was chromatographed on silica gel, eluting with 1:4 ethyl acetate:hexane to give Compound No. 63 (0.15 g). M$^+$=236; $^1$H NMR (CDCl$_3$): δ2.45(2H m); 3.20(2H,t); 4.2–4.4(1H,m); 7.00(1H,d); 8.39(1H,d) (oil).

Step 2: Preparation of 2-[(4,4-difluoro-3-butenyl)thio]-4-phenoxypyrimidine (Compound No. 74)

The foregoing Compound No. 63 (0.15 g) was stirred in dimethyl formamide (DMF) (5 cm$^3$) containing potassium carbonate (0.175 g) and phenol (0.063 g) was added. The reaction mixture was stirred at ambient temperature for 8 hours and left to stand overnight, after which it was poured into water and the product was extracted into diethyl ether. The organic layer was washed with saturated brine and the residue after evaporation of solvent under reduced pressure was chromatographed on silica gel, eluting with 1:4 ethyl acetate:hexane, to give Compound No. 74 (0.15 g). M$^+$=294; $^1$H NMR (CDCl$_3$): δ2.20(2H,m); 2.89(2H,t); 3.9–4.1(1H, m); 6.53(1H,d); 7.12(2H,d); 7.25(1H,m); 7.41(2H,m); 8.33 (1H,d) (oil).

EXAMPLE 5C

This example illustrates the dehydration of a pyrimidine carboxamide to the corresponding nitrile.

Compound No. 81 (see Example 4C) (0.2 g) and phosphorous oxychloride (1 cm$^3$) were heated together at 80° C. for ninety minutes. The mixture was cooled, added to crushed ice and the product extracted with diethyl ether. The organic layer was washed with water and saturated sodium bicarbonate solution and dried over magnesium sulfate. Evaporation of solvent under reduced pressure gave a dark oil (0.18 g) which was chromatographed on silica gel eluting with 1:4 ethyl acetate:hexane to give 4-cyano-2-[(4,4-difluoro-3-butenyl)thio]-pyrimidine (Compound No. 42) (0.167 g). M$^+$=227; $^1$H NMR (CDCl$_3$): δ2.40–2.50(2H,m); 3.20(2H,t); 4.20–4.38(1H,m); 7.28(1H,d); 8.72(1H,d) (oil).

EXAMPLE 5D

This example illustrates the hydrolysis of a pyrimidine carboxamide to the corresponding carboxylic acid.

Compound No. 81 (see Example 4C) (0.205 g) was heated in 1M aqueous sodium hydroxide (1 cm$^3$) at 90° C. for one hour. The basic solution was cooled and washed with ethyl acetate, discarding the organic layer. The aqueous layer was acidified to pH 1 with 2M hydrochloric acid and cooled to 5° C. for one hour to complete the precipitation of product. The solid obtained was recovered by filtration and dried by azeotroping with acetone to give 2-[(4,4-difluoro-3-butenyl) thio]-4-pyrimidinecarboxylic acid (Compound No. 82) as a beige solid (0.163 g) mp 164.5°–165.5° C. M$^+$=246; $^1$H NMR (CDCl$_3$): δ2.42–2.52(2H,m); 3.30(2H,t); 4.56–4.76 (1H,m); 7.74(1H,d); 8.94(1H,d).

EXAMPLE 5E

This example illustrates the esterification of a pyrimidine carboxylic acid to the corresponding carboxylic ester.

Compound No. 82 (see Example 5D) (0.19 g) was added in methanolic hydrogen chloride (5 cm$^3$ of a saturated solution) and the flask was stoppered and left to stand for 72 hours. All the solid starting material had dissolved. The solution was evaporated to dryness at reduced pressure and the residue was dissolved in ethyl acetate. The organic solution was washed with saturated aqueous sodium bicarbonate and dried over magnesium sulfate. Evaporation of solvent under reduced pressure gave an oil which was chromatographed on silica gel, eluting with 1:4 ethyl acetate:hexane to give methyl 2-[(4,4-difluoro-3-butenyl) thio]-4-pyrimidinecarboxylate (Compound No. 83) (0.154 g). M$^+$=260; $^1$H NMR (CDCl$_3$): δ2.40–2.54(2H m); 3.24 (2H,t); 4.00(3H,s); 4.22–4.40(1H,m); 7.64(1H,d); 8.74(1H, d).

EXAMPLE 5F

A general procedure for preparing 2-[(4,4-difluoro-3-butenyl)thio]-substituted pyrimidines from (4,4-difluoro-3-butenyl)-thiourea in a standard ring-forming reaction with 1,3-dicarbonyl compounds or their synthetic equivalents is illustrated by the following preparation of Compound No. 92.

(4,4-difluoro-3-butenyl)-thiourea 4-methyl-benzenesulfonate salt (see Example 3D) (0.47 g) and methyl 4-methoxyacetoacetate (0.203 g) (Aldrich Chemical Co.) were stirred together in water (4 cm$^3$) and N-benzyl-trimethylammonium hydroxide (0.3 cm$^3$) was added. The mixture was heated at 70° C. for seven hours, cooled, poured into water and product was extracted with ethyl acetate. The organic layer was washed with saturated brine, dried over magnesium sulfate and the solvent was removed under reduced pressure to give an off-white solid. This was purified by chromatography on silica gel, eluting with 3:7 ethyl acetate:hexane to remove non-polar impurities and 1:1 ethyl acetate:hexane to give 2-[(4,4-difluoro-3-butenyl)thio]-6-methoxymethyl-4(3H)-pyrimidinone (Compound No. 92) (0.21 g). M$^+$=262; $^1$H NMR (CDCl$_3$): δ2.40(2H,m); 3.2(2H, t); 3.48(3H,s); 4.17–4.35(1H,m); 4.29(2H,s); 6.32(1H,s) (white solid mp 124.5°–125.3° C.).

EXAMPLE 5G

Compound No. 90 according to the invention was prepared as follows.

Ethyl benzoyl acetate (3 cm$^3$) and N,N-dimethylformamide diethyl acetal (3.1 cm$^3$) were stirred together under a nitrogen atmosphere at the ambient temperature for 24 hours. Low-boiling material was removed by evaporation under reduced pressure, leaving a residue (3.4 g). A portion of this residue (0.66 g) was dissolved in ethanol (15 cm$^3$). (4,4-difluoro-3-butenyl)-thiourea 4-methyl-benzenesulfonate salt (see Example 3D) (1.0 g) and N-ethyl piperidine (0.6 cm$^3$) were added and the mixture was heated under reflux for 12 hours. The solution was cooled and the ethanol removed by evaporation under reduced pressure. The residue was diluted with water and the product extracted into ethyl acetate. The organic layer was washed with saturated brine, dried over magnesium sulfate and evaporated under reduced pressure to give a yellow gum which was chromatographed on silica gel, eluting with 15:85 ethyl acetate:hexane to give ethyl 2-[(4,4-difluoro-3-butenyl)thio]-4-phenyl-5-pyrimidinecarboxylate (Compound No. 90) (0.53 g). M$^+$=350; $^1$H NMR (CDCl$_3$): δ1.11(3H,t); 2.49(2H, m); 3.24(2H,t); 4.21(2H,q); 4.2–4.4(1H,m); 7.41–7.60(5H, m); 8.90(1H,s) (oil).

Compound No. 87 was prepared from 1-benzoyl acetone using an analogous procedure to that given above for Compound No. 90.

(i) 5-benzoyl-2-[(4,4-difluoro-3-butenyl)thio]-4-methylpyrimidine (Compound No. 87). M$^+$=320; $^1$H NMR (CDCl$_3$): δ2.40–2.55(2H,m); 3.24(2H,t); 4.2–4.4(1H,m); 7.5 (2H,t); 7.65(1H,m) 7.80(2H,d); 8.48(1H,s).

EXAMPLE 5H

This example illustrates the hydrolysis of a pyrimidine carboxylic ester to the corresponding carboxylic acid.

Compound No. 90 (see Example 5G) (0.25 g) was stirred with lithium hydroxide monohydrate (0.059 g) in water (8 cm$^3$) and tetrahydrofuran (8 cm$^3$) at ambient temperature for 18 hours. The basic reaction mixture was then partitioned between water and diethyl ether, the organic layer being discarded. The aqueous layer was acidified with 2M hydrochloric acid and the product extracted into ethyl acetate. The organic layer was washed with saturated brine and dried over magnesium sulfate. The solvent was removed by evaporation under reduced pressure to give 2-[(4,4-difluoro-3-butenyl)thio]-4-phenyl-5-pyrimidinecarboxylic acid (Compound No. 91) (0.15 g). M$^+$=322; $^1$H NMR (CDCl$_3$): δ2.49(2H,q); 3.23(2H,t); 4.2–4.4(1H,m); 7.49(3H,m); 7.62 (2H,m); 9.00(1H,s) (white solid mp 129°–130° C.).

EXAMPLE 5I

This example illustrates the hydrolysis of a pyrimidinecarboxaldehyde acetal to the corresponding aldehyde.

Compound No. 62 (see Example 4B (i)) (0.5 g), p-toluenesulfonic acid (0.15 g) and toluene (10 cm$^3$) were heated under reflux for 13 hours, and left to cool to the ambient temperature for a further 72 hours. The solvent was removed by evaporation under reduced pressure and the residue was chromatographed on silica gel, eluting with 1:4 ethyl acetate:hexane. The product, 2-[(4,4-difluoro-3-butenyl)thio]-4-pyrimidinecarboxyaldehyde (Compound No. 80) was a yellow oil (0.112 g). $^1$H NMR (CDCl$_3$): δ2.42–2.56(2H,m); 3.26(2H,t); 4.24–4.40(1H,m); 7.46(1H, d); 8.78(1H,d); 9.96(1H,s).

EXAMPLE 6

The following process illustrates a method suitable for the preparation of compounds according to the invention in which the sulfur atom of the 4,4-difluoro-3-butenylthio substituent of the corresponding unoxidised compound (prepared according to the procedures of Examples 4 or 5) is oxidised to sulfoxide (sulfinyl) or sulfone (sulfonyl). In general, the use of one equivalent of oxidising agent leads predominantly to the formation of the corresponding sulfoxide product and two equivalents lead to the formation of the sulfone. Mixtures of the oxidised products are frequently obtained, and these may be readily separated by standard techniques such as column chromatography.

Preparation of Compounds Nos. 96 and 97 from Compound No. 4.

Compound No. 4 (see Example 4B) (0.68 g) was stirred at ambient temperature in tert-butanol (15 cm$^3$) and magnesium monoperoxyphthalic acid hexahydrate (Aldrich Chemical Co.) (1.21 g in 10 cm$^3$ water) was added over a period of five minutes. After one hour, tlc indicated that the starting material had been consumed. The reaction mixture was poured into water and the product was extracted into ethyl acetate. The organic layer was washed with saturated sodium bicarbonate solution and dried over magnesium sulfate. Evaporation of solvent under reduced pressure gave an oil (0.73 g) which was chromatographed on silica gel, eluting first with 1:4 ethyl acetate:hexane to remove less polar impurities, then dichloromethane to give 2-[(4,4-difluoro-3-butenyl)sulfonyl]-4-phenylpyrimidine (Compound No. 97) (0.189 g). mp 103°–104.5° C. $^1$H NMR (CDCl$_3$): δ2.60–2.74(2H,m); 3.68(2H,t); 4.24–4.42(1H,m); 7.52–7.62(3H,m); 7.94(1H,d); 8.14–8.20(2H,m); 8.94(1H, d). Finally, elution with ethyl acetate gave 2-[(4,4-difluoro-3-butenyl)sulfinyl]-4-phenylpyrimidine (Compound No. 96) (0.409 g). $^1$H NMR (CDCl$_3$): δ2.34–2.50(1H,m); 2.58–2.76 (1H,m); 3.16–3.36(2H,m); 4.18–4.36(1H,m); 7.5–7.6(3H, m); 7.78(1H,d); 8.14–8.20(2H,m); 8.92(1H,d); (oil).

The following compound according to the invention was prepared by the above procedure of Example 6:

(i) 2-[(4,4-difluoro-3-butenyl)sulfinyl]-4-(2,2,2-trifluoroethoxy)-pyrimidine (Compound No. 66) from Compound No. 65 (see Example 4D (iii)). $^1$H NMR (CDCl$_3$): δ2.28–2.46(1H,m); 2.54–2.70(1H,m); 3.06–3.28(2H,m); 4.16–4.32(1H,m); 4.80–5.02(2H,m); 6.96(1H,d); 8.68(1H, d) (oil).

EXAMPLE 7

The activity of the compounds of formula (I) was determined using a variety of pests. The pests were treated with a liquid composition containing 500 parts per million (ppm)

by weight of the compound unless otherwise stated. The compositions were made by dissolving the compound in acetone and diluting the solutions with water containing 0.01% by weight of a wetting agent sold under the trade name "SYNPERONIC" NX until the liquid composition contained the required concentration of the compound. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the medium and the pests with the compositions. The mortality of the pests was then assessed at periods usually varying from one to three days after the treatment.

The results of the tests are presented in Table II for each of the compounds at the rate in parts per million given in the second column. The results indicate a grading of mortality designated as A, B or C wherein A indicates less than 50% mortality, B indicates 50–79% mortality and C indicates 80–100% mortality (figures indicate knockdown control for test MDb); - indicates that either the compound was not tested or no meaningful result was obtained.

Information regarding the pest species, the support medium or food, and the type and duration of the test is given in Table II. The pest species is designated by a letter code.

TABLE II

| COM-POUND | RATE OF APPLICATION ppm | TU | MPa | MDa | MDb | HV | SE | DB |
|---|---|---|---|---|---|---|---|---|
| | | | | (see Table III) | | | | |
| 1  | 500 | C | C | A | A | C | A | C |
| 5  | 500 | C | C | A | B | C | A | B |
| 13 | 500 | C | C | A | A | C | A | A |
| 16 | 500 | C | C | — | B | B | B | B |
| 29 | 500 | C | C | A | C | A | A | B |
| 36 | 500 | C | C | A | B | C | A | C |
| 37 | 500 | C | C | B | B | C | A | A |
| 43 | 500 | C | C | A | A | C | B | C |
| 46 | 500 | C | C | A | A | B | A | — |
| 61 | 500 | C | C | A | B | A | A | B |
| 63 | 500 | C | C | — | A | A | A | C |
| 64 | 500 | A | C | A | A | A | A | — |
| 65 | 500 | B | C | A | A | B | A | A |
| 66 | 500 | C | C | A | A | C | A | B |
| 67 | 500 | C | C | A | — | A | A | C |
| 68 | 500 | A | C | A | B | A | C | C |
| 69 | 500 | C | C | A | A | A | A | A |
| 70 | 500 | C | C | A | A | C | A | — |
| 71 | 500 | C | C | A | A | A | A | C |
| 72 | 500 | A | C | A | B | C | A | A |
| 73 | 500 | C | C | — | — | A | A | A |
| 74 | 500 | C | C | A | — | A | A | C |
| 75 | 500 | C | C | — | A | A | A | A |
| 76 | 500 | C | C | A | A | C | C | B |
| 77 | 500 | C | C | A | A | B | A | C |
| 95 | 500 | C | C | A | A | B | A | C |

TABLE III

| CODE LETTERS | TEST SPECIES | SUPPORT MEDIUM FOOD | TYPE OF TEST | DURATION (days) |
|---|---|---|---|---|
| TU | Tetranychus urticae (spider mite) | French bean leaf | Contact | 3 |
| MPa | Myzus persicae (green peach aphid) | Chinese Cabbage leaf | Contact | 3 |
| MDa | Musca domestica (houseflies - adults) | Cotton wool/ sugar | Knock-down | 15 mins |
| MDb | Musca domestica (houseflies - adults) | Cotton wool/ sugar | Contact | 2 |
| HV | Heliothis virescens (Tobacco budworm - larva) | Soya leaf | Residual | 5 |
| SE | Spodoptera exigua (lesser armyworm - larva) | Cotton leaf | Residual | 5 |
| DB | Diabrotica balteata (banded cucumber beetle - larva) | Filter paper/ maize seed | Residual | 2 |

"Contact" test indicates that both pests and medium were treated, "Residual" indicates that the medium was treated before infestation with the pests and "in vitro" indicates that the pest was suspended in an aqueous medium containing the treatment.

EXAMPLE 8

This Example further illustrates the insecticidal activity of compounds of Formula (I) according to the invention.

In Table IV, further results are given for the activity of test compounds against four species. at various rates of application. The test procedures and details for tests TU (Tetranychus urticae, contact), MPa Myzus persicae, contact) and DB (Diabrotica balteata, contact) are as described in Example 8 and Table III. Application rates are shown in the table heading for each test type. The test procedure for Test MPb (Myzus persicae, systemic) was as follows:

Upward systemicity of the test compounds was evaluated against the peach potato aphid, Myzus persicae by soil drenching 2–3 week old radish plants (cv. Cherrybelle) at 10 ppm. Plants with 1st true leaves approximately 2×1 cm were used. The cotyledons, growing point and 1 true leaf were removed. The soil was covered with a clear lid. 12–18 mature aphids were added to each plant 1 day before treatment. On the treatment day each pot was placed in a 250 ml plastic pot with a fluon band to prevent aphid escape. Each pot was treated with 10 ml of chemical solution (prepared in 1% ethanol and acetone (1:1) and 0.01% Synperonic NP8—ICI Chemicals & Polymers). Each treatment was replicated 3 times. The treated plants were transferred to a constant environment room at 20 C., 60% relative humidity and a 16 hour photoperiod. The mortality was assessed at 3 and 5 days after treatment (DAT).

Results in Table IV are expressed as % Control observed. - indicates that either the compound was not tested or no meaningful result was obtained.

TABLE IV

| | SPECIES | | | |
|---|---|---|---|---|
| COMPOUND NO. | TU (25 ppm) | MPA (27 ppm) | DB (25 ppm) | MPB (10 ppm) |
| 1  | 17 | 6   | 97 | 95 |
| 5  | —  | 100 | —  | 94 |
| 13 | 41 | 14  | —  | 65 |
| 29 | 26 | 38  | —  | —  |

TABLE IV-continued

| COMPOUND NO. | TU (25 ppm) | MPA (27 ppm) | DB (25 ppm) | MPB (10 ppm) |
|---|---|---|---|---|
| 36 | — | 100 | 83 | 43 |
| 65 | — | 72 | — | 67 |
| 66 | 34 | 14 | — | 100 |
| 68 | — | — | 53 | — |
| 69 | — | 67 | — | 86 |

EXAMPLE 9

This Example illustrates the nematicidal properties of the compounds of Formula (I) according to the invention.

Three tests were established to demonstrate nematicidal efficacy.

Test A: In vitro test.

In vitro activity against the root knot nematode, *Meloidogyne incognita* was evaluated by treatment of a suspension of freshly-hatched (0–24 hours old) juveniles of *M. incognita* with a liquid composition containing the test chemical at test rates of 1.65–0.02 ppm. To preparae the compositions, the test chemicals were diluted to double the rate required in 1% ethanol and acetone (1:1) and 99% deionised water. 0.5 cm$^3$ of chemical solution was added to 0.5 cm$^3$ of nematode suspension (δ200 nematodes/cm$^3$) in a glass vial. Each treatment was replicated twice. The vials were capped and left for 72 hours in a Constant Temperature room at 23° C. in the dark. The numbers of dead and alive nematodes were then counted under a stereomicroscope and the number of dead nematodes is expressed in Table V as a percentage of the total nematode count (% Dead).

Test B: Soil drench test.

Activity against the root knot nematode, *Meloidogyne incognita*, was evaluated by applying the candidate nematicide as a drench solution to 2 week old cucumber plants (cultivar Telegraph) and infesting the soil with nematodes. 10 cm$^3$ of a solution comprising the test compound, dissolved in a 1% solvent solution (50:50 acetone and ethanol), and 0.05% SYNPERONIC NP8 (ICI Chemicals & Polymers) in distilled water was added to each plant such that the final soil concentration was 2 ppm. Each treatment was replicated twice. The cucumber plants were inoculated 48 hours after treatment with a 2 cm$^3$ suspension of freshly hatched juveniles at a concentration of 350 nematodes per cm$^3$. The test was maintained at 25° C. with a 16 hour photoperiod for 9 days. The roots of each plant were assessed for percentage root-knot reduction relative to an untreated, infested control and the results are recorded in Table V as % knot reduction compared to the control.

Test C: Foliar application test.

Downward systemicity of test chemicals was evaluated by spraying 4–6" high tomato plants (cultivar Moneymaker) to incipient run-off with a chemical solution at 1000 ppm. Soil contamination was prevented by wrapping plastic film around the base of the stem and over the soil. The chemical solution (diluted in 5% ethanol and acetone (1:1) and 5% sucrose) was sprayed onto the plants (5 cm$^3$/plant) at 15 p.s.i. (103.4 kPa) with a hand operated sprayer. Each treatment was replicated three times. 48 hours after treatment each plant was inoculated with 700 freshly-hatched (0–24 hours old) juveniles of *Meloidogyne incognita* (root knot nematode). Plants were maintained in a constant environment at 25° C. for 21 days and watered from the base of the pot. Root-knot reduction relative to an untreated, infested control was then assessed and the results are recorded in Table V as % knot reduction compared to the control.

TABLE V

| COMPOUND NO | TEST A (% Dead) 1.65 ppm | TEST B (% Knot reduction) 2.0 pm | TEST C (% Knot reduction) 1000 ppm |
|---|---|---|---|
| 1 | 94.3 | 98.2 | — |
| 3 | 5.1 | 40.0 | — |
| 4 | 93.8 | 0 | — |
| 5 | 98.1 | 99.5 | 40.8 |
| 13 | 94.1 | 93.2 | — |
| 16 | 93.5 | 0.1 | — |
| 29 | 93.6 | 100 | — |
| 36 | 95.4 | 0.1 | — |
| 37 | 85.6 | 0.3 | — |
| 46 | 98.1 | 90.3 | — |
| 47 | 6.5 | 0 | — |
| 61 | 56.6 | 0 | — |
| 62 | 14.8 | 0 | — |
| 63 | 94.7 | 80 | — |
| 64 | 4.7 | 69.0 | — |
| 65 | 76.2 | 88.4 | — |
| 66 | 94.1 | 99.7 | 47.5 |
| 67 | 97.7 | — | — |
| 69 | 96.2 | 90.1 | — |
| 70 | 6.2 | 93.6 | — |
| 73 | 91.6 | 83.0 | — |
| 74 | 94.5 | — | — |
| 76 | 56.6 | 0.3 | — |
| 77 | 95.5 | 0 | — |
| 78 | 98.7 | 0 | — |
| 81 | 57.7 | — | — |
| 90 | 94.5 | — | — |
| 93 | 96.5 | — | — |
| 94 | 95.7 | 0 | — |
| 95 | 100 | 63.6 | — |

— indicates that the compound was not tested in this test

EXAMPLE 10

The spectrum of nematicidal activity of compounds of Formula (I) according to the invention was investigated in contact assays. Greatest activity was seen against endoparasitic species such as the root-knot nematode *Meloidogyne incognita*, the potato cyst nematode *Globodera rostochiensis*, the sugarbeet cyst nematode *Heterodera schachtii* and the reniform nematode *Rotylenchulus reniformis*. Activity was evident, but to a lesser extent, against migratory species such as Aphelenchoides spp and Ditylenchus spp. This indicates that compounds according to the invention have the potential for broad spectrum control of nematode species representative of different habitats and feeding habits.

The following examples demonstrate formulations suitable for applying the compounds of the present invention. The amount of ingredient is expressed in parts by weight or grams per liter as indicated. * indicates a trademark.

EXAMPLE 11

This example demonstrates granules suitable for soil application. The granules can be made be standard techniques such as impregnation, coating, extrusion or agglomeration.

|  |  | % w/v |
|---|---|---|
| Impregnated granule: | Active ingredient | 5 |
|  | Wood Rosin | 2.5 |
|  | Gypsum granules (20–40 mesh) | 92.5 |
| Coated granule: | Active ingredient | 0.5 |
|  | 'Solvesso'* 200 | 0.4 |
|  | Calcium carbonate granules (30–60 mesh) | 99.1 |
| Slow release granule: | Active ingredient | 10 |
|  | Polyvinylacetate/vinyl chloride copolymer latex | 5 |
|  | Attapulgus granules | 85 |

EXAMPLE 12

This example demonstrates formulations for use as a spray. The compounds can be formulated as wettable powders, water dispersible granules, suspension concentrates, emulsifiable concentrates, emulsions or microcapsule suspensions for application diluted in water.

|  |  | g/l |
|---|---|---|
| Emulsifiable concentrate: | Active ingredient | 250 |
|  | Calcium dodecyl-benzene sulphonate | 50 |
|  | Nonyl phenol ethoxylate | 50 |
|  | Alkylbenzene solvent | to 1 liter |
|  |  | % w/w |
| Wettable powder: | Liquid active ingredient | 40 |
|  | lignosulphonate dispersant | 5 |
|  | silica | 25 |
|  | sodium lauryl sulphate | 3 |
|  | china clay (kaolin) | 27 |
| Microcapsule suspension: | Liquid active ingredient | 250 |
|  | toluene diisocyanate polymethylene polyphenyl isocyanate | 10 |
|  |  | 20 |
|  | nonyl phenol ethoxylate | 6 |
|  | lignosulphonate dispersant | 15 |
|  | xanthan gum | 1 |
|  | bentonite | 10 |
|  | biocide 'Proxel'* | 0.1 |
|  | sodium carbonate | 5 |
|  | water | to 1 liter |

The microcapsule suspensions can be used as a spray, soil drench or as an intermediate to prepare slow release granules for application to the soil.

|  |  | g/l |
|---|---|---|
| Suspension concentrate: | Solid active ingredient | 400 |
|  | lignosulphonate dispersant | 50 |
|  | sodium lauryl sulphate | 30 |
|  | xanthan gum | 1 |
|  | biocide 'Proxel'* | 0.1 |
|  | bentonite | 10 |
|  | water | to 1 liter |

EXAMPLE 13

This example demonstrates formulations suitable for use as seed treatments in conventional application machinery.

|  |  | % w/w |
|---|---|---|
| Dry seed treatment: | Active ingredient | 20 |
|  | dodecyl benzene | 3 |
|  | Rubine Toner (dyestuff) | 2.7 |
|  | Talc | 53.3 |
|  | Silica | to 100% |

The suspension concentrate and microcapsule suspension of Example 5 can be used as flowable concentrates for seed treatment.

EXAMPLE 14

This example demonstrates the formulation of the compounds for electrostatic spraying.

|  | g/l |
|---|---|
| Active ingredient | 200 |
| N-methylpyrrollidone | 50 |
| Soyabean oil | 120 |
| 'Solvesso'* 200 | to 1 liter |

EXAMPLE 15

This Example illustrates the fungicidal properties of the compounds of Formula (I) according to the invention.

The test compounds were formulated either by bead milling with aqueous Dispersol T or as a solution in acetone or acetone/ethanol. They were then diluted to 100 ppm in water, and 2.5 cm$^3$ aliquots were placed in Petri dishes. These were further diluted to 25 ppm (active ingredient) with Potato Dextrose Agar.

The dishes were inoculated with the fungal pathogens shown in Table V, using either spore suspensions or mycelial plugs. These were then incubated at an appropriate temperature (19°–25° C.) and growth assessments made after 2 days as a percentage of the level of disease present on the untreated control medium. The results are expressed in Table VI as a POCO (Percentage of Control) value calculated according to the formula given below and rounded to the nearest figure on the following standard scale: 0, 1, 3, 5, 10, 15, 20, 30, 60, 90.

$$POCO = \frac{\text{disease level on treated medium}}{\text{disease level on untreated control}}$$

TABLE V

| Test Organisms | |
|---|---|
| Abbreviations | Latin Name |
| Ch | *Pseudocercosporella herpotrichoides* |
| Sn | *Septoria nodorum* |
| Bc | *Botrytis cinerea* |
| Pc | *Phytophthora cinnamomi* |
| Po | *Pyricularia oryzae* |
| Tc | *Thanatephorus cucumeris* |
| An | *Aspergillus niger* |
| Au | *Aureobasidium pullulans* |
| Gr | *Gliocladium roseum* |
| Pe | *Penicillium pinophilum* |

TABLE VI

| Compound No | Ch | Sn | Bc | Pc | Po | Tc | An | Au | Gr | Pe |
|---|---|---|---|---|---|---|---|---|---|---|
| 5 | 0 | 50 | 90 | 50 | 15 | 50 | 90 | 90 | 90 | 90 |
| 65 | 3 | 50 | 3 | 90 | 3 | 50 | 50 | 15 | 90 | 90 |
| 66 | 0 | 3 | 50 | 50 | 0 | 50 | 90 | 0 | 15 | 50 |

CHEMICAL FORMULAE
(IN DESCRIPTION)

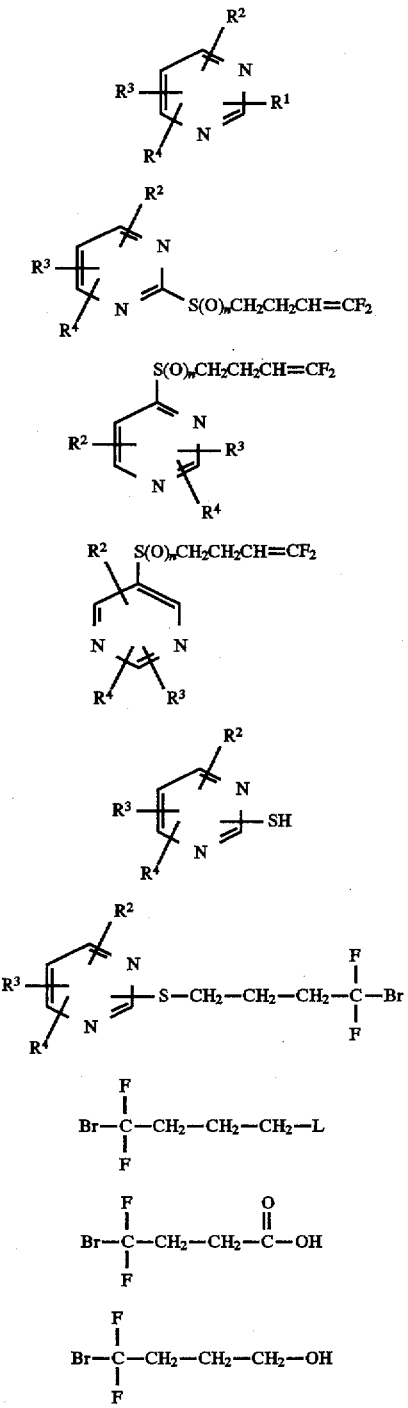

-continued
CHEMICAL FORMULAE
(IN DESCRIPTION)

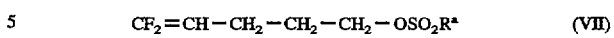 (VII)

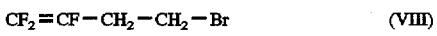 (VIII)

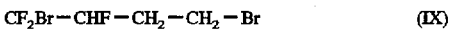 (IX)

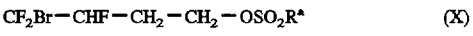 (X)

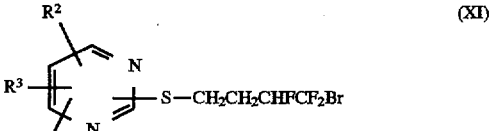 (XI)

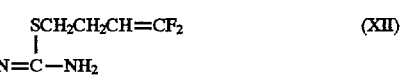 (XII)

We claim:
1. Compound of Formula (I)

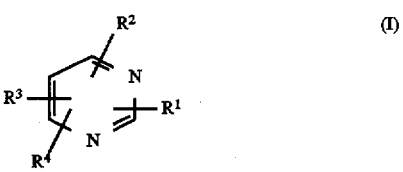 (I)

wherein $R^1$ is $-S(O)_n CH_2 CH_2 CH = CF_2$;

n is selected from 0, 1 and 2;

$R^2$, $R^3$, and $R^4$ are independently selected from hydrogen, alkyl, alkenyl, alkynyl, cycloalkyl, alkylcycloalkyl, optionally substituted aryl, optionally substituted arylalkyl, optionally substituted aryloxy, optionally substituted arylalkoxy, alkoxy, alkenyloxy, alkynyloxy, hydroxyalkyl, alkoxyalkyl, alkylthio, alkenylthio, alkynylthio, haloalkyl, haloalkenyl, haloalkynyl, haloalkoxy, haloalkenyloxy, haloalkynyloxy, haloalkylthio, haloalkenylthio, haloalkynylthio, halogen, hydroxy, cyano, nitro, $-NR^5R^6$, $-NR^7COR^8$, $-NR^9SO_2R^{10}$, $-N(SO_2-R^{11})(SO_2-R^{12})$, $-COR^{13}$, $-CONR^{14}R^{15}$, $-COOR^{16}$, $-OCOR^{17}$, $-OSO_2R^{18}$, $-SO_2NR^{19}R^{20}$, $-SO_2R^{21}$, $-SOR^{22}$, $-CSNR^{23}R^{24}$, $-SiR^{25}R^{26}R^{27}$, $-OCH_2CO_2R^{28}$, $-OCH_2CH_2CO_2R^{29}$, $-CONR^{30}SO_2R^{31}$, $-SO_2Z$, or an adjacent pair or $R^2$, $R^3$ and $R^4$ when taken together form a fused 5- or 6-membered carbocyclic or heterocyclic ring;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ are independently selected from hydrogen, alkyl, alkenyl, alkynyl, haloalkyl, haloalkenyl, haloalkynyl, optionally substituted aryl and optionally substituted arylalkyl, with the proviso that when one of $R^5$ and $R^6$ is hydrogen, the other of $R^5$ and $R^6$ is not optionally substituted aryl; and Z is halogen.

2. Compound as claimed in claim 1 wherein $R^1$ is $-S(O)_n CH_2 CH_2 CH = CF_2$;

n is 0, 1 or 2;

$R^2$, $R^3$, and $R^4$ are independently selected from hydrogen, $C_{1-6}$ alkyl $C_{2-6}$ alkenyl, $C_{2-6}$ alkynyl, $C_{3-6}$ cycloalkyl, $C_{4-7}$ alkylcycloalkyl, phenyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, phenyl-$C_{1-2}$-alkyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, phenoxy optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, phenyl-$C_{1-2}$-alkoxy optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, $C_{1-6}$ alkoxy, $C_{2-6}$ alkenyloxy, $C_{2-6}$ alkynyloxy, hydroxy-$C_{1-6}$-alkyl, $C_{2-6}$ alkoxyalkyl, $C_{3-6}$ dialkoxyalkyl, $C_{1-6}$ alkylthio, $C_{2-6}$ alkenylthio, $C_{2-6}$ alkynylthio, $C_{1-6}$ haloalkyl, $C_{2-6}$ haloalkenyl, $C_{2-6}$ haloalkynyl, $C_{1-6}$ haloalkoxy, $C_{2-6}$ haloalkenyloxy, $C_{2-6}$ haloalkynyloxy, $C_{1-6}$ haloalkylthio, $C_{2-6}$ haloalkenylthio, $C_{2-6}$ haloalkynylthio, halogen, hydroxy, cyano, nitro, —$NR^5R^6$, —$NR^7COR^8$, —$NR^9SO_2R^{10}$, —$N(SO_2—R^{11})(SO_2—R^{12})$, —$COR^{13}$, —$CONR^{14}R^{15}$, —$COOR^{16}$, —$COOR^{16}$, —$OCOR^{17}$, —$OSO_2R^{18}$, —$SO_2NR^{19}R^{20}$, —$SO_2R^{21}$, —$SOR^{22}$, —$CSNR^{23}R^{24}$, —$SiR^{25}R^{26}R^{27}$, —$OCH_2CO_2R^{28}$, —$OCH_2CH_2CO_2R^{29}$, —$CONR^{30}SO_2R^{31}$, —$SO_2Z$, or an adjacent pair of $R^2$, $R^3$ and $R^4$ when taken together form a fused 5- or 6-membered heterocyclic ring containing two oxygen atoms and optionally substituted with one or more halogen or methyl groups, or a 5- or 6-membered carbocyclic ring;

$R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}, R^{27}, R^{28}, R^{29}, R^{30}$ and $R^{31}$ are independently selected from hydrogen, $C_{1-6}$ alkyl, $C_{2-6}$ alkenyl, $C_{2-6}$ alkynyl, $C_{1-6}$ haloalkyl, $C_{2-6}$ haloalkenyl, $C_{2-6}$ haloalkynyl, phenyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, and benzyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro; and Z is fluoro, chloro or bromo.

3. Compound as claimed in claim 1 wherein:

$R^1$ is —$S(O)_nCH_2CH_2CH=CF_2$;

n is 0, 1 or 2;

$R^2, R^3$, and $R^4$ are independently selected from hydrogen, $C_{1-4}$ alkyl, $C_{2-6}$ alkenyl, $C_{2-6}$ alkynyl, $C_{3-5}$ cycloalkyl, $C_{4-7}$ alkylcycloalkyl, phenyl optionally substituted by chloro, fluoro, methyl, ethyl, methoxy, trifluoromethoxy, trifluoromethyl or nitro, benzyl optionally substituted by chloro, fluoro, methyl, ethyl, methoxy, trifluoromethoxy, trifluoromethyl or nitro, phenoxy optionally substituted by chloro, fluoro, methyl, trifluoromethyl or nitro, benzoxy optionally substituted by chloro, fluoro, methyl, trifluoromethyl or nitro, 4-nitrobenzoxy, $C_{1-4}$ alkoxy, $C_{2-6}$ alkenyloxy, $C_{2-4}$ alkynyloxy, hydroxy-$C_{1-4}$-alkyl, $C_{2-4}$ alkoxyalkyl, $C_{3-6}$ dialkoxyalkyl, $C_{1-4}$ alkylthio, $C_{2-6}$ alkenylthio, $C_{2-4}$ alkynylthio, $C_{1-4}$ fluoroalkyl, $C_{1-4}$ chloroalkyl, $C_{2-6}$ fluoroalkenyl, $C_{2-4}$ chloroalkenyl, $C_{1-4}$ fluoroalkoxy, $C_{1-4}$ chloroalkoxy, $C_{2-6}$ fluoroalkenyloxy, $C_{2-4}$ chloroalkenyloxy, $C_{1-4}$ fluoroalkylthio, $C_{1-4}$ chloroalkylthio, $C_{2-6}$ fluoroalkenylthio, $C_{2-4}$ chloroalkenylthio, chloro, fluoro, bromo, iodo, hydroxy, cyano, nitro, amino, —$NHR^5$ where $R^5$ is $C_{1-4}$ alkyl, —$NR^5R^6$ where $R^5$ and $R^6$ are $C_{1-4}$ alkyl, —$NR^7COR^8$ where $R^7$ is hydrogen and $R^8$ is hydrogen or $C_{1-4}$ alkyl, —$NR^9SO_2R^{10}$ where $R^9$ is hydrogen and $R^{10}$ is $C_{1-4}$ alkyl, —$N(SO_2—R^{11})(SO_2—R^{12})$ where $R^{11}$ and $R^{12}$ are $C_{1-4}$ alkyl, —$COR^{13}$ where $R^{13}$ is hydrogen or $C_{1-4}$ alkyl, —$CONR^{14}R^{15}$ where $R^{14}$ and $R^{15}$ are hydrogen or $C_{1-4}$ alkyl, —$COOR^{16}$ where $R^{16}$ is hydrogen, $C_{1-4}$ alkyl, $C_{1-4}$ haloalkyl or $C_{2-6}$ fluoroalkenyl, —$OCOR^{17}$ where $R^{17}$ is $C_{1-4}$ alkyl, —$OSO_2R^{18}$ where $R^{18}$ is $C_{1-4}$ alkyl, —$SO_2NR^{19}R^{20}$ where $R^{19}$ and $R^{20}$ are hydrogen or $C_{1-4}$ alkyl, —$SO_2R^{21}$ where $R^{21}$ is $C_{1-4}$ alkyl or $C_{1-4}$ haloalkyl, —$SOR^{22}$ where $R^{22}$ is $C_{1-4}$ alkyl or $C_{1-4}$ haloalkyl, —$CSNR^{23}R^{24}$ where $R^{23}$ and $R^{24}$ are hydrogen or $C_{1-4}$ alkyl, —$SiR^{25}R^{26}R^{27}$ where $R^{25}, R^{26}$ and $R^{27}$ are $C_{1-4}$ alkyl, —$OCH_2CO_2R^{28}$ where $R^{28}$ is $C_{1-4}$ alkyl, —$CONR^{30}SO_2R^{31}$ where $R^{30}$ is hydrogen and $R^{31}$ is $C_{1-4}$ alkyl, —$SO_2F$, or where an adjacent pair of $R^2, R^3$ and $R^4$ taken together are —$(CH_2)_3$—, —$(CH_2)_4$—, —$CH=CH—CH=CH$—, or —$O—CH_2—O$— optionally substituted with one or two halogen atoms.

4. Compound according to claim 1 wherein $R^1$ is —$S(O)_nCH_2CH_2CH=CF_2$;

n is 0, 1 or 2;

$R^2, R^3$, and $R^4$ are independently selected from hydrogen, ethyl, allyl, but-3-enyl, 3-methylbut-3-enyl, ethynyl, propargyl, cyclopropyl, 1-methylcyclopropyl, phenyl, 4-chlorophenyl, 4-fluorophenyl, 3-trifluoromethylphenyl, 4-trifluoromethylphenyl, 4-methylphenyl, 4-nitrophenyl, benzyl, 4-chlorobenzyl, 4-fluorobenzyl, 3-trifluoromethylbenzyl, 4-trifluoromethylbenzyl, 4-methylbenzyl, 4-nitrobenzyl, phenoxy, 4-chlorophenoxy, 4-fluorophenoxy, 3-trifluoromethylphenoxy, 4-trifluoromethylphenoxy, 4-methylphenoxy, 4-nitrophenoxy, benzoxy, 4-chlorobenzoxy, 4-fluorobenzoxy, 3-trifluoromethylbenzoxy, 4-trifluoromethylbenzoxy, 4-methylbenzoxy 4-nitrobenzoxy, methoxy, ethoxy, iso-propoxy, n-propoxy, sec-butoxy, allyloxy, but-3-enyloxy, 3-methylbut-3-enyloxy, propargyloxy, hydroxymethyl, 2-hydroxyethyl, 3-hydroxypropyl, methoxymethyl, ethoxymethyl, methoxyethyl, dimethoxymethyl, methylthio, ethylthio, allylthio, but-3-enylthio, 3-methylbut-3-enylthio, propargylthio, fluoromethyl, difluoromethyl, trifluoromethyl, 2-fluoroethyl, chloromethyl, dichloromethyl, trichloromethyl, 2,2-difluoroethenyl, 3,4,4-trifluorobut-3-enyl, 4,4-difluorobut-3-enyl, 4,4-difluoro-3-methylbut-3-enyl, 3,3-dichloroprop-2-enyl, 2-chloroprop-2-enyl, fluoromethoxy, difluoromethoxy, trifluoromethoxy, 2-fluoroethoxy, 1,1,2,2-tetrafluoroethoxy, trichloromethoxy, 3,4,4-trifluorobut-3-enyloxy, 4,4-difluorobut-3-enyloxy, 4,4-difluoro-3-methylbut-3-enyloxy, 2-chloroprop-2-enyloxy, 3,3-dichloroprop-2-enyloxy, fluoromethylthio, difluoromethylthio, trifluoromethylthio, 2-fluoroethylthio, trichloromethylthio, 3,4,4-trifluorobut-3-enylthio, 4,4-difluorobut-3-enylthio, 4,4-difluoro-3-methylbut-3-enylthio, 2-chloroprop-2-enylthio, 3,3-dichloroprop-2-enylthio, chloro, fluoro, bromo, iodo, hydroxy, cyano, nitro, amino, methylamino, ethylamino, dimethylamino, diethylamino, formamido, acetamido, propionamido, benzamido, methanesulphonamido, ethanesulphonamido, N,N-di-(methanesulphonyl) amino, N,N-di-(ethanesulphonyl)amino, formyl, acetyl, propionyl, carboxamido, N-methylcarboxamido, N-ethylcarboxamido, N,N-dimethylcarboxamido, N-methyl-N-ethylcarboxamido, N,N-diethylcarboxamido, N-(n-propyl)carboxamido, —COOH, methoxycarbonyl, ethoxycarbonyl, 2-fluoroethoxycarbonyl, 3,4,4-trifluorobut-3-enyloxycarbonyl, 3-methyl-4,4-difluorobut-3-enyloxycarbonyl, 4,4-difluorobut-3-enyloxycarbonyl, methoxycarbonyloxy, ethoxycarbonyloxy, methanesulphonyloxy, ethanesulphonyloxy, —SO$_2$NH$_2$, N,N-dimethylaminosulphonyl, N,N-diethylaminosulphonyl, methanesulphonyl, ethanesulphonyl, trifluoromethanesulphonyl, methanesulphinyl, ethanesulphinyl, trifluoromethanesulphinyl, —CSNH$_2$, —CSNH(CH$_3$), —CSN(CH$_3$)$_2$, trimethylsilyl, —OCH$_2$CO$_2$CH$_3$, —OCH$_2$CO$_2$CH$_2$CH$_3$, N-(methanesulphonyl) carboxamido or —SO$_2$F, or where an adjacent pair of R$^2$, R$^3$ and R$^4$ taken together are —(CH$_2$)$_3$—, —(CH$_2$)$_4$—, —CH=CH—CH=CH—, —O—CH$_2$—O—, —O—CHF—O—, —O—CF$_2$—O—, —O—CH(CH$_3$)—O—, —O—C(CH$_3$)$_2$—O— or —O—(CH$_2$)$_2$—O—.

5. Compound as claimed in claim 1 wherein
R$^1$ is —S(O)$_n$CH$_2$CH$_2$CH=CF$_2$;
n is 0, 1 or 2;
R$^2$ R$^3$ and R$^4$ are independently selected from hydrogen, C$_{1-4}$ alkyl, phenyl optionally substituted by chloro, fluoro, methyl, ethyl, methoxy, trifluoromethoxy, trifluoromethyl or nitro, C$_{1-4}$ alkoxy, C$_{1-4}$ fluoroalkyl, C$_{1-4}$ fluoroalkoxy, chloro, or —COOR$^{16}$ where R$^{16}$ is C$_{1-4}$ alkyl.

6. Compound as claimed in claim 5 wherein
R$^1$ is —S(O)$_n$CH$_2$CH$_2$CH=CF$_2$;
n is 0, 1 or 2;
R$^2$, R$^3$ and R$^4$ are independently selected from hydrogen, methyl ethyl, phenyl, 4-chlorophenyl, 4-fluorophenyl, 3-trifluoromethylphenyl, 4-trifluoromethylphenyl, 4-methylphenyl, 4-nitrophenyl, methoxy, ethoxy, iso-propoxy, n-propoxy, sec-butoxy, fluoromethyl, difluoromethyl, trifluoromethyl, 2-fluoroethyl, fluoromethoxy, difluoromethoxy, trifluoromethoxy, 2-fluoroethoxy, 1,1,2,2-tetrafluoroethoxy, chloro, methoxycarbonyl or ethoxycarbonyl.

7. Compound as claimed in claim 1 of Formula (IA) or Formula (IB)

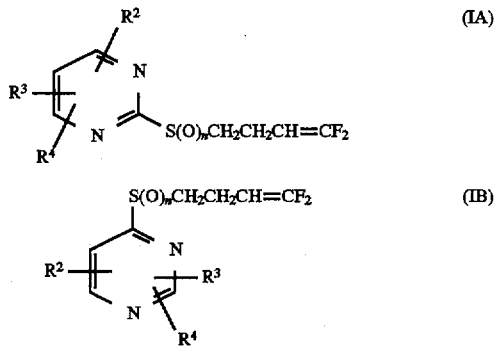

wherein R$^2$–R$^4$, n and Z have any of the meanings given in claim 1.

8. Compound as claimed in claim 7 wherein R$^2$–R$^4$, n and Z have any of the meanings given in claim 1, with the proviso that at least one of the groups R$^2$–R$^4$ is hydrogen.

9. Compound according to claim 1 wherein n is 0.

10. A nematicidal, insecticidal or acaricidal composition comprising a nematicidally, insecticidally or acaricidally effective amount of a compound of formula (I) as claimed in claim 1 and an inert diluent or carrier material.

11. A method for killing or controlling nematode, insect or acarid pests which comprises applying to the locus of the pest or to a plant or seed susceptible to attack by the pest an effective amount of a compound as claimed in claim 1.

12. A fungicidal composition comprising a fungicidally effective amount of a compound as claimed in claim 1 and a fungicidally acceptable carrier or diluent.

13. A method of combating fungi which comprises applying to a plant, to a seed of a plant or to the locus of the plant or seed a fungicidally effective amount of a compound as claimed in claim 1.

* * * * *